US012629248B2

(12) United States Patent
Zhao et al.

(10) Patent No.: US 12,629,248 B2
(45) Date of Patent: May 19, 2026

(54) INTRAOCULAR LENS IMPLANTER AND PRELOADED TYPE INTRAOCULAR LENS IMPLANTATION DEVICE

(71) Applicant: EYEBRIGHT MEDICAL TECHNOLOGY (BEIJING) CO., LTD, Beijing (CN)

(72) Inventors: Lijun Zhao, Beijing (CN); Jiangbing Xie, Beijing (CN)

(73) Assignee: EYEBRIGHT MEDICAL TECHNOLOGY (BEIJING) CO., LTD., Beijing (CN)

( * ) Notice: Subject to any disclaimer, the term of this patent is extended or adjusted under 35 U.S.C. 154(b) by 1136 days.

(21) Appl. No.: 17/425,151

(22) PCT Filed: Jan. 30, 2019

(86) PCT No.: PCT/CN2019/074001
§ 371 (c)(1),
(2) Date: Jul. 22, 2021

(87) PCT Pub. No.: WO2020/151021
PCT Pub. Date: Jul. 30, 2020

(65) Prior Publication Data
US 2022/0117725 A1    Apr. 21, 2022

(30) Foreign Application Priority Data

Jan. 25, 2019    (CN) .......................... 201910074809.1
Jan. 25, 2019    (CN) .......................... 201910075668.5

(51) Int. Cl.
*A61F 2/16*        (2006.01)

(52) U.S. Cl.
CPC ............ *A61F 2/167* (2013.01); *A61F 2/1678* (2013.01)

(58) Field of Classification Search
CPC ....... A61F 2/167; A61F 2/1672; A61F 2/1678
See application file for complete search history.

(56) References Cited

U.S. PATENT DOCUMENTS 7,156,854 B2    1/2007 Brown et al.
9,572,710 B1    2/2017 Kudo et al.
(Continued)

FOREIGN PATENT DOCUMENTS

CN      102307543 A      1/2012
CN      104127264 A      11/2014
(Continued)

*Primary Examiner* — Sarah W Aleman
*Assistant Examiner* — Rachel S Highland
(74) *Attorney, Agent, or Firm* — Shumaker, Loop & Kendrick, LLP; John A. Miller

(57) ABSTRACT

An intraocular lens implanter and a preloaded type intraocular lens implantation device, which can improve the operational reliability of the injection member so as to improve the operational reliability of rolling or folding of the intraocular lens in an expected direction. In the intraocular lens implanter the inner cavity of the implantation head is provided with a guide portion, where the guide portion has a shape approaching the movement route of the push pin from rear to front, so that the push pin can push the movable piece of the pressing plate on the guide portion, and the movable piece applies downward force to the push pin in turn, thereby the push pin performs the injection operation under the state that the head portion of the push pin keeps in contact with the lower surface of the inner cavity of the implantation head.

16 Claims, 17 Drawing Sheets

(56)                    References Cited

U.S. PATENT DOCUMENTS 9,655,718 B2 *    5/2017   Kudo ...................... A61F 2/167
2016/0193042 A1      7/2016   Hoffmann et al.

FOREIGN PATENT DOCUMENTS

CN          104414774  A      3/2015
CN          104414774  B     12/2017
CN          107920891  A      4/2018
EP           2161005  B1     12/2016

* cited by examiner

INTRAOCULAR LENS IMPLANTER AND PRELOADED TYPE INTRAOCULAR LENS IMPLANTATION DEVICE

CROSS-REFERENCE TO RELATED APPLICATIONS

This application is a National Stage application of International Application No. PCT/CN2019/074001 filed on Jan. 30, 2019, which claims priority to Chinese Application No. 201910075668.5 filed Jan. 25, 2019 and Chinese Application No. 201910074809.1 filed Jan. 25, 2019.

BACKGROUND

Field

The disclosure relates to an intraocular lens implanter and a preloaded type intraocular lens implantation device.

Discussion of the Related Art

An intraocular lens is an artificial lens. A technique for replacing a natural lens in a human eye that becomes clouded due to cataract disease by implanting an intraocular lens in cataract surgery has been widely practiced. The intraocular lens is generally constituted of a centrally located circular optic portion and supporting portion at the periphery, with upper and lower surfaces of the optic portion being referred to as an optic portion upper surface and an optic portion lower surface, respectively. Because of different materials of the intraocular lens, the intraocular lenses are classified into a rigid intraocular lens in which the optic portion is formed of a hard material such as PMMA or the like, and a soft intraocular lens in which the optic portion is formed of a flexible material such as silicone elastomer, hydrogel, soft acrylate and the like. The intraocular lens made of the flexible material is also often referred to as a foldable intraocular lens.

When the rigid intraocular lens is used, a surgical incision made on the cornea to implant the intraocular lens must have a width approximately the same as the diameter of the optic portion of the lens. Whereas the intraocular lens made of the soft material (also often referred to as the foldable intraocular lens) can be inserted into the eye through a small incision (typically 2-3 mm) after being folded or rolled to reduce its area. The folded or rolled intraocular lens can automatically unfold after entering the eye.

After the folded or rolled intraocular lens enters the eye, it is ensured that the lens does not damage a rear capsule of the eye in the unfolding process, and meanwhile, the unfolding process of the lens should be convenient for an operator to observe and assist the unfolding operation of the lens when the unfolding of the lens is not smooth, so that the lower surface of the optic portion of the unfolded intraocular lens is adhered to the rear capsule of the eye. In summary, it is desired that the folding or rolling of the intraocular lens is performed in an expected direction, in which the lower surface of the optic portion of the intraocular lens is folded or rolled toward the upper surface of the optic portion.

In order to implant an intraocular lens into an eye, it is necessary to use a dedicated intraocular lens implanter such as the intraocular lens implanter disclosed in, any of patent documents 1 to 6, which has an inner cavity design for folding the intraocular lens and a slender tubular passage structure design. By using the dedicated intraocular lens implanter, the soft intraocular lens can be implanted into a human eye through a small incision which is less than 3 mm.

Two conditions need to be met for ensuring that the intraocular lens is smoothly pushed out in the implanter and the folded or rolled intraocular lens unfolds in the expected direction after being pushed out. On condition is that a head portion of a push pin of the implanter is reliably contacted with a side edge surface of the optic portion of the intraocular lens in the process of injecting the intraocular lens, without the problem that the head portion of the push pin is separated from the side edge surface of the optic portion of the intraocular lens and moves to the upper surface or the lower surface of the optic portion of the intraocular lens due to movement resistance of the intraocular lens in the process of injecting the intraocular lens. The other condition is that the intraocular lens is folded or rolled in the correct expected direction in the process of injecting the intraocular lens, so that the folded intraocular lens injected into the eye can be ensured to be unfolded in the expected direction.

In the intraocular lens implanter, the intraocular lens is usually placed on a lens holder in a state where the upper surface of the optic portion faces upward and the lower surface of the optic portion faces downward, so that the lower surface of the optic portion is in contact with the surface of the lens holder. The intraocular lens leaves the lens holder and enters an inner cavity channel of an implantation head under the action of the injection of the push pin of the preloaded implanter. During the movement of the intraocular lens in the inner cavity channel of the implantation head, because the expected folding direction of the intraocular lens is to be folded from the lower surface side to the upper surface side (from bottom to top), the smaller the gap between the lower surface of the optic portion of the intraocular lens and the lower surface of the inner cavity channel of the implantation head, the more reliable the movement in which the intraocular lens is folded or rolled in the expected direction under the action of the specially designed inner cavity channel of the implantation head. And meanwhile, during the injection of the intraocular lens by the push pin, the smaller the gap between the lower bottom surface of the push pin and the lower surface of the inner cavity channel of the implantation head, the smaller the risk of the push pin coming out of contact with the edge side of the optic portion of the intraocular lens and moving to the upper surface of the optic portion, and the higher the reliability of the injection.

In other words, when the intraocular lens in the preloaded implanter moves away from the lens holder and enters the inner cavity channel of the implantation head and moves in the inner cavity channel under the action of the push pin, if the lower surface of the optic portion of the intraocular lens and the lower bottom surface of the push pin are always in contact with the lower surface of the inner cavity channel of the implantation head without gap (that is, to maintain the state of so-called bottom-supporting movement), the operational reliability of the intraocular lens being folded or rolled in the expected direction under the action of the specially designed inner cavity channel of the implantation head and the operational reliability of the push pin pushing the intraocular lens to move are the highest.

In the intraocular lens implanter disclosed in any of the above patent documents, there is room for improvement in terms of ensuring the operational reliability of the push pin (injection member) pushing the intraocular lens to move and the operational reliability of the intraocular lens being folded or rolled in the expected direction, and there is a risk that the head portion of the push pin comes out of contact with the side edge surface of the optic portion of the intraocular lens and moves to the upper surface of the optic portion of the intraocular lens or the lower surface of the optic portion due to the influence of the injection resistance of the intraocular lens during the injecting of the push pin. In addition, in the technique disclosed in the above patent documents, the influence of the flow of viscoelastic agent on the change of the state of the front supporting portion when the viscoelastic agent is injected is not sufficiently considered, and there is a problem that the folding of the front supporting portion during the pushing is unstable and the reliability is to be improved.

Documents of the Prior Art

Patent document 1: EP2161005B1
Patent document 2: CN107920891A
Patent document 3: U.S. Pat. No. 7,156,854B2
Patent document 4: CN104414774B
Patent document 5: CN104127264A
Patent document 6: U.S. Pat. No. 9,572,710B1

SUMMARY

In view of the above, the present disclosure is proposed. A first object of the present disclosure is to provide an intraocular lens implanter capable of improving operational reliability of an injection member to thereby improve operational reliability of rolling or folding of an intraocular lens in an expected direction. A second object of the present disclosure is to provide a preloaded type intraocular lens implantation device which improves operational reliability of folding of a front supporting portion of the intraocular lens.

In order to achieve the above objects, the intraocular lens implanter according to the present disclosure is configured to implant an intraocular lens having an optic portion into a human eye, the optic portion of the intraocular lens having a first optic portion surface and a second optic portion surface which face away from each other, the intraocular lens implanter comprising: an implanter body having an intraocular lens holder for holding the intraocular lens; an implantation head having a transition portion for causing the intraocular lens to undergo at least a deformation in which the intraocular lens is rolled from the side of the first optic portion surface toward the side of the second optic portion surface when the intraocular lens passes through, and a nozzle portion for implanting the intraocular lens passed through the transition portion into a human eye; an injection member for injecting the intraocular lens from the intraocular lens holder into the human eye via the transition portion and the nozzle portion, wherein further comprising: a biasing means, which applies a force in a direction from the side of the second optic portion surface to the side of the first optic portion surface to the injection member in at least a part of a process that the injection member performs an injection operation.

With the above configuration, since the biasing means is provided to apply a force in a direction from the side of the second optic portion surface to the side of the first optic portion surface to the injection member in at least a part of the process that the injection member performs the injection operation, the injection member can be pushed by the biasing means to the surface of the inner cavity of the implantation head on the same side as the first optic portion surface of the intraocular lens, so that the injection member can perform the injection operation in a state of contacting or approximately contacting the surface. In this way, the operational reliability of the injection member can be improved, the operational reliability of rolling or folding of the intraocular lens in an expected direction can be improved, and the above firth object can be achieved.

In the present disclosure, the biasing means includes a biasing member that applies the force to the injection member by being sandwiched between the injection member and a surface of an inner cavity of the transition portion.

In addition, the biasing member also applies the force to the injection member by being sandwiched between the injection member and a surface of an inner cavity of the implanter body.

In this way, the operational reliability of the injection member can be effectively ensured at the initial stage of the injection operation.

In the present disclosure, the biasing member, which applies force in a direction from the side of the second optic portion surface to the side of the first optic portion surface to the injection member by being sandwiched between the injection member and a surface of an inner cavity of the transition portion in a process that the injection member injects the intraocular lens to move in an inner cavity of the transition portion, at least when the intraocular lens leaves the intraocular lens holder, where the sandwiching refers to a state where the biasing member and a part of the injection member for sandwiching the biasing member contact each other and overlap in a direction perpendicular to the first optic portion surface or the second optic portion surface, that is, the biasing member, the injection member and the inner cavity of the transition portion are colinear along a single line which is perpendicular to the first optic portion surface or the second optic portion surface. In the present disclosure, an end of the biasing member facing the nozzle portion is configured to orientate the first optic portion surface before being sandwiched and when it is not in contact with the upper surface of the inner cavity of the transition portion.

In the present disclosure, it is preferable that the biasing member is configured to be movable in a direction of the injection operation, the surface of the inner cavity of the transition portion of the implantation head is provided with a guide portion, which has a shape approaching a movement route from rear to front along which the injection member moves when performing the injection operation, and guides the biasing member so that when moving forward, the biasing member produces displacement in a direction approaching the movement route of the injection member to be able to apply the force.

In addition, the guide portion is constituted of a single slope, or at least two slopes with different inclination angles, or a curved surface. In the present disclosure, it is preferable that, in the case where the guide portion is formed of a single slope, an inclination angle of the slope with respect to the movement route of the injection member is 1.5 to 25 degree, 2.5 to 11 degree, or 3.5 to 6.5 degree.

In the present disclosure, it is preferable that the biasing member has a movable portion and a fixed portion, the fixed portion and the injection member are engaged with each other in a manner capable of moving together in the direction of the injection operation in an initial state before the injection operation, and the movable portion protrudes forward in the direction of the injection operation with respect to the injection member, the movable portion is driven to move on account that the fixed portion moves together along with the injection operation of the injection member, and when the movable portion moves to a predetermined position (for example, the position that overlaps with the second slope in the embodiment), the biasing member is stopped.

In the present disclosure, it is preferable that the fixed portion of the biasing member is provided with a stopper protrusion, the guide portion on the surface of the inner cavity of the transition portion of the implantation head is provided with a guide groove, the stopper protrusion can enter the guide groove to be guided by the guide groove when the biasing member moves, and the stopper protrusion is blocked by an end surface of an end of the guide groove when the stopper protrusion moves to the end of the guide groove, so that the biasing member is stopped.

In the present disclosure, it is preferable that the biasing member is constituted by a flat pressing plate including a fixed piece as the fixed portion and a movable piece as the movable portion. In the present disclosure, it is preferable that the movable piece is provided with a protrusion contactable with the guide portion of the transition portion of the implantation head.

With the above configuration, the movable piece contacts with the surface (guide portion) of the transition portion through the protrusion, so that the contact area can be reduced, and the situation that the movement of the movable piece is blocked due to large friction can be avoided.

In the disclosure, the protrusion can be in a semi-cylindrical shape, a discoid shape, a ring shape extending along the edge of the movable piece or more than two strips which are parallel to each other.

In the present disclosure, it is preferable that the fixed piece is provided with a biasing protrusion protruding toward the injection member for applying the force to the injection member. By adopting the configuration, the operational reliability of the injection member can be effectively ensured in the initial stage of the injection.

In the present disclosure, it is preferable that the fixed piece is connected to the movable piece via a connecting piece formed by a thin part.

In the present disclosure, it is preferable that a front end portion of the injection member in a direction of the injection operation has a lens contacting portion and an extension protruding forward from the lens contacting portion, wherein the lens contacting portion is located on the side of the second optic portion surface of the intraocular lens, and the extension is located on the side of the first optic portion surface.

By adopting the above configuration, the reliability of the injection operation can be further increased, and the risk that the injection member separates from the side surface edge of the optic portion and moves to the second optic portion surface of the optic portion because the optic portion of the intraocular lens is subjected to the friction resistance during the injection is avoided.

The biasing member is preferably soft. A protrusion may be formed on an upper surface of the front end portion of the injection member.

In addition, the intraocular lens implanter according to the present disclosure is preferably a preloaded type intraocular lens implanter in which the intraocular lens is preloaded to the intraocular lens holder.

In the present disclosure, it is preferable that the pressing means is capable of applying a force in a direction from the side of the second optic portion surface to the side of the first optic portion surface to the optic portion of the intraocular lens.

The disclosure also provides a preloaded type intraocular lens implantation device comprising the intraocular lens implanter and an intraocular lens preloaded inside the intraocular lens implanter, wherein the intraocular lens has an optic portion and a front supporting portion disposed in front of the optic portion, on the intraocular lens implanter, a guide member for the front supporting portion is disposed at a position between the optic portion and the front supporting portion, and is capable of guiding the front supporting portion to produce upward displacement when the front supporting portion are moved rearward. With the above configuration, since the guide member for the front supporting portion is provided between the optic portion and the front supporting portion, the guide member can guide the front supporting portion to produce upward displacement when it moves rearward for example due to an impact of the viscoelastic agent, so that the operational reliability of folding of the front supporting portions onto the upper surface of the optic portion can be improved, and the second object of the present disclosure can be achieved.

In the present disclosure, it is preferable that the preloaded type intraocular lens implantation device further comprises a retaining mount, wherein the intraocular lens implanter is provided with a pin hole which is positioned between the optic portion of the intraocular lens and a front end portion of the front supporting portion in a front-rear direction, the retaining mount is provided with a retaining pin, which is inserted into the intraocular lens implanter through the pin hole and is positioned between the optic portion of the intraocular lens and the front end portion of the front supporting portion to retain the intraocular lens to move forward, and the guide member for the front supporting portion is the retaining pin. With the above configuration, the guide member for the front supporting portion is formed by the retaining pin for retaining the intraocular lens to move forward, so that the number of parts can be reduced, the structure can be simplified, and the manufacturing cost can be reduced.

In the present disclosure, it is preferable that a guide surface is formed on a front surface of the retaining pin facing the front supporting portion, the guide surface being constituted by a slope extending obliquely upward and rearward. With the above configuration, since the front surface of the retaining pin facing the front end portion of the front supporting portion has the guide surface formed by the slope extending obliquely upward and rearward, when the front supporting portion moves rearward due to, for example, an impact of the viscoelastic agent, the front supporting portion is lifted upward under the guidance of the guide surface extending obliquely upward and rearward, so that the operational reliability of folding of the front supporting portion onto the upper surface of the optic portion can be improved.

The advantages and novel features characterizing the present disclosure are pointed out with particularity in the claims annexed hereto and forming a part hereof. However, for a better understanding of the disclosure, its advantages, and the objects obtained by its use, reference should be made to the drawings which form a further part hereof, and to the following detailed description, in which one or more preferred embodiments of the disclosure are illustrated and described.

BRIEF DESCRIPTION OF THE DRAWINGS

FIGS. 8a to 8d are partially enlarged perspective views schematically showing the head of the push pin according to the first embodiment, wherein FIG. 8a is a perspective view seen from the oblique front, FIG. 8b is a side view, FIG. 8c is a perspective view seen from substantially above, and FIG. 8d is a perspective view seen from the lower surface of the push pin;

FIG. 10a-10e are sectional views schematically showing the implantation head in the first embodiment in different sections, wherein FIG. 10a-10e are sectional views at lines P-P, N-N, M-M, L-L, K-K shown in FIG. 9, respectively;

REFERENCE NUMERALS

1—intraocular lens implanter; 2—implantation head; 2a—nozzle portion of the implantation head; 2b—transition portion of the implantation head; 3—implanter body; 3a—external thread; 4—spiral tube; 5—intraocular lens; 6—optic portion of the intraocular lens; 7a—front supporting portion of the intraocular lens; 7b—rear supporting portion of the intraocular lens; 8—pressing plate; 8a—movable piece of the pressing plate; 8b—connecting piece for the pressing plate; 8c—fixed piece of the pressing plate; 8d—push pin stopper ribs on the fixed piece; 8e—protrusion on the upper surface of the movable piece; 8f—protrusion on the lower surface of the fixed piece; 8g—stopper protrusion on the upper surface of the fixed piece; 9—push pin; 9a—lens contacting portion of the push pin; 9b—extension of the push pin; 9c—protrusion (first protrusion) on the lower surface of the front end portion of the push pin; 9f—protrusion (second protrusion) on the upper surface of the front end portion of the push pin; 10—push rod; 11—intraocular lens holder at front-end of implanter body; 12—rear section of implanter body; 13—guide portion on the upper surface of inner cavity of transition portion of the implantation head; 14—snap-fit projection on the pressing plate; 15—snap-fit recess on the push pin; 16—guide groove on the upper surface of the implantation head; 30—inner packaging member; 40—retaining mount; 41—holder of the retaining mount; 42—retaining pin of the retaining mount.

DETAILED DESCRIPTION OF THE EMBODIMENTS

Hereinafter, embodiments of the present disclosure will be described in detail with reference to the drawings.

First Embodiment

The first embodiment of the present disclosure will be described below with reference to FIGS. 1 to 10e.

Figure 1:
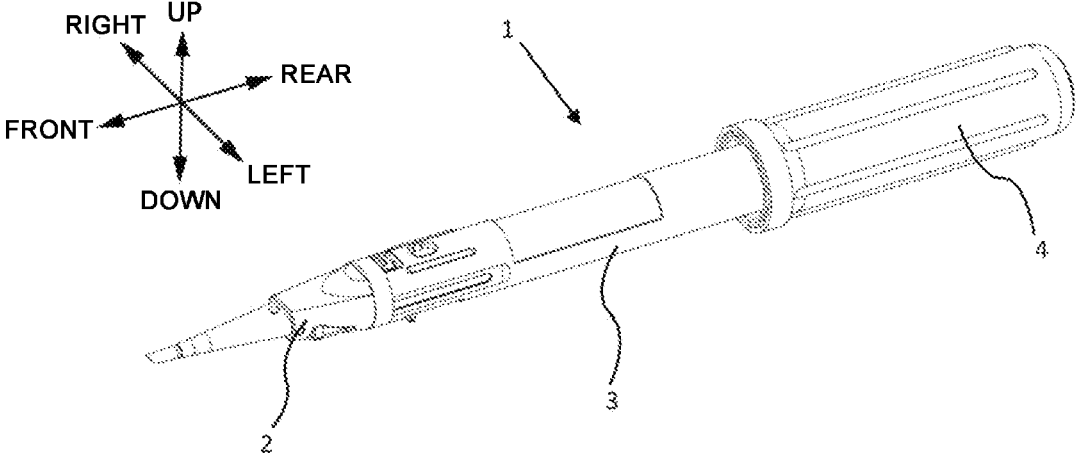
FIG. 1 is a perspective view schematically showing the overall structure of an intraocular lens implanter according to a first embodiment of the present disclosure.
Figure 2:
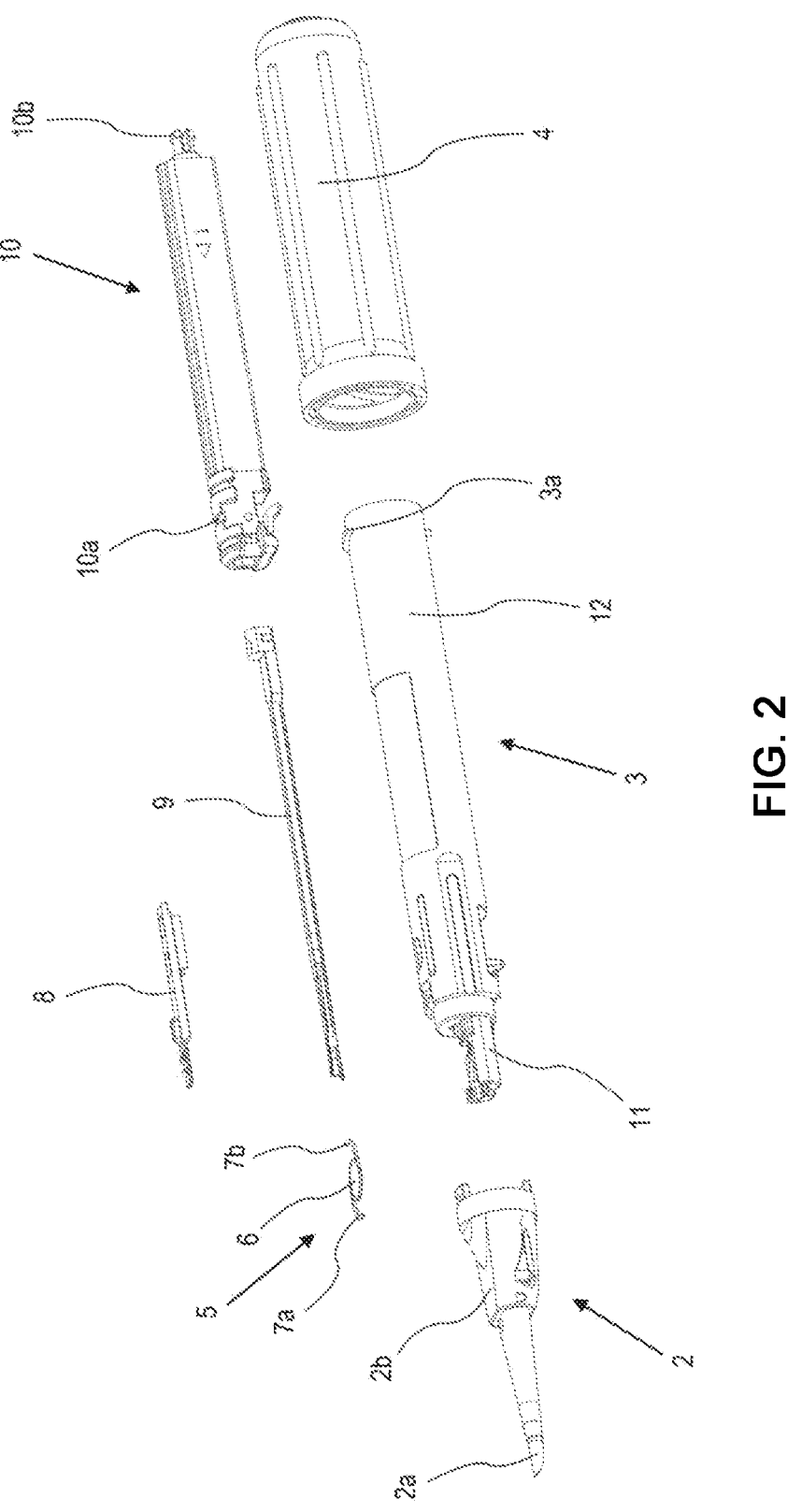
FIG. 2 is an exploded view schematically showing the intraocular lens implanter.
Figure 3:
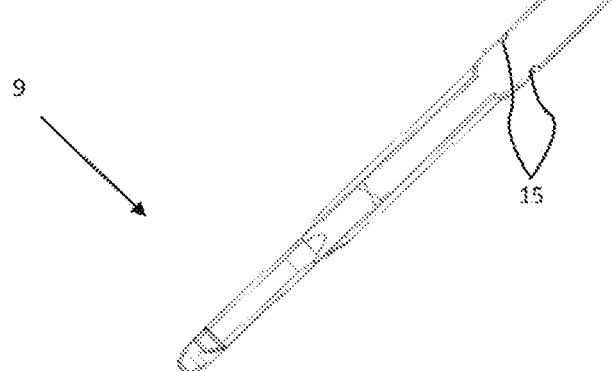
FIG. 3 is an enlarged perspective view schematically showing a head of a push pin in the first embodiment.
Figure 4A:
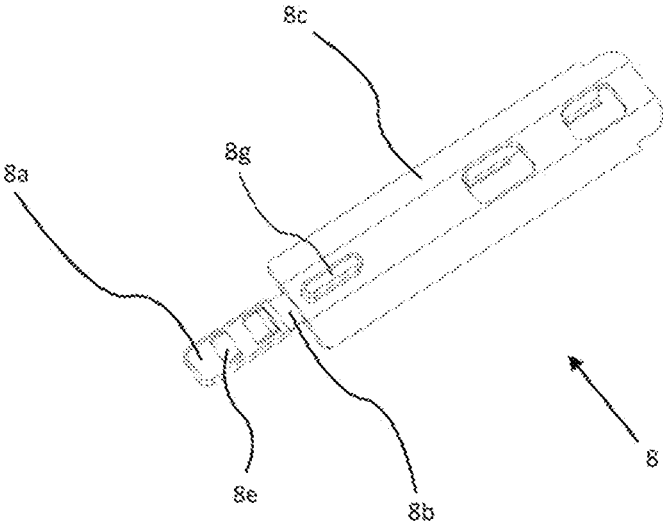
FIG. 4a is a perspective view schematically showing a front surface of a pressing plate in the first embodiment.
Figure 4B:
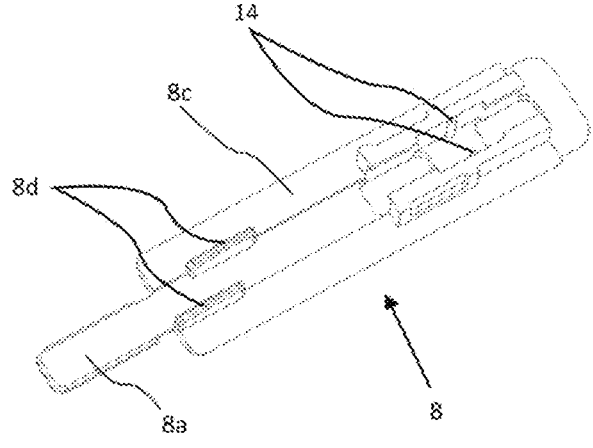
FIG. 4b is a perspective view schematically showing a rear surface of the pressing plate in the first embodiment.
Figure 5A:
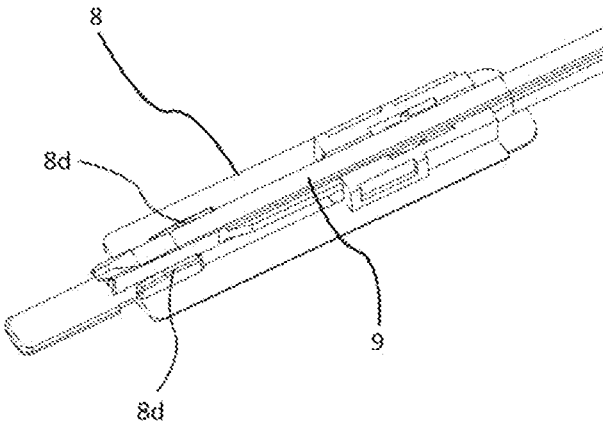
FIG. 5a is a perspective view schematically showing the assembly of the push pin and the pressing plate in the first embodiment.
Figure 5B:
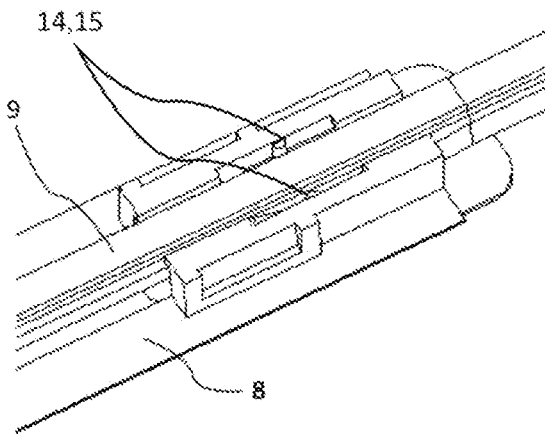
FIG. 5b is a partially enlarged perspective view schematically showing the assembly of the push pin and the pressing plate in the first embodiment.
Figure 6:
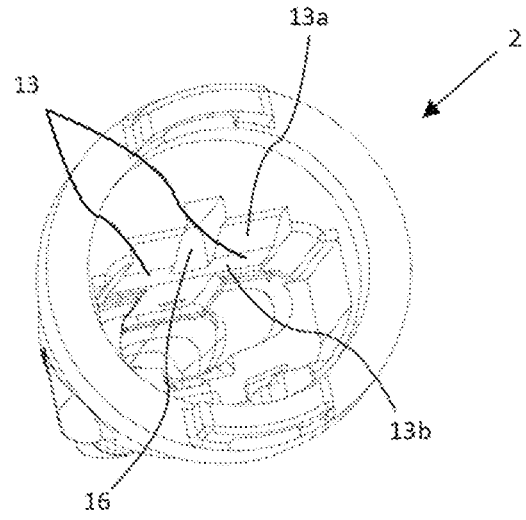
FIG. 6 is a perspective view schematically illustrating an upper surface of an inner cavity of a transition portion of an implantation head in the first embodiment.
Figure 7A:
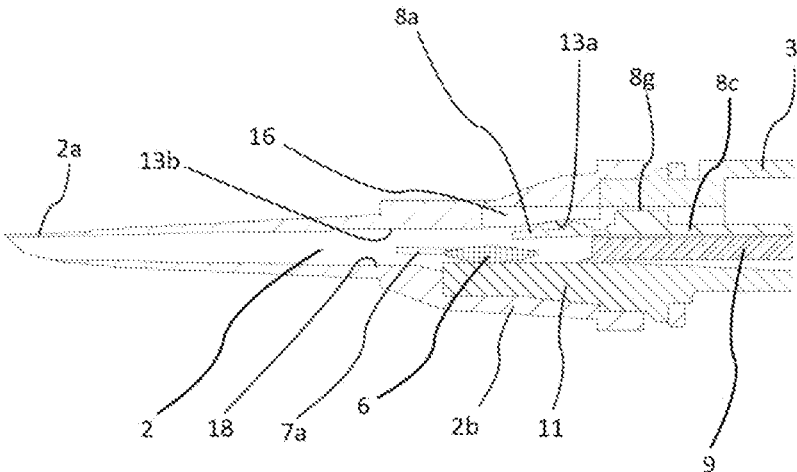
FIG. 7a is an enlarged partial cross-sectional view schematically showing a front end of the intraocular lens implanter according to the first embodiment when the assembly of the intraocular lens implanter is completed or at the beginning of the injection (initial state)
Figure 7B:
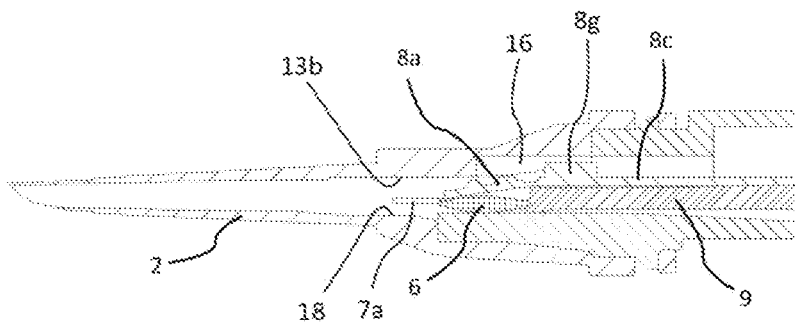
FIG. 7b is an enlarged partial cross-sectional view schematically showing the front end of the intraocular lens implanter according to the first embodiment in a state that the push pin and the pressing plate of the intraocular lens implanter move together so that the lens-contacting portion of the head of the push pin is in contact with the side surface of the optic portion of the intraocular lens.
Figure 7C:
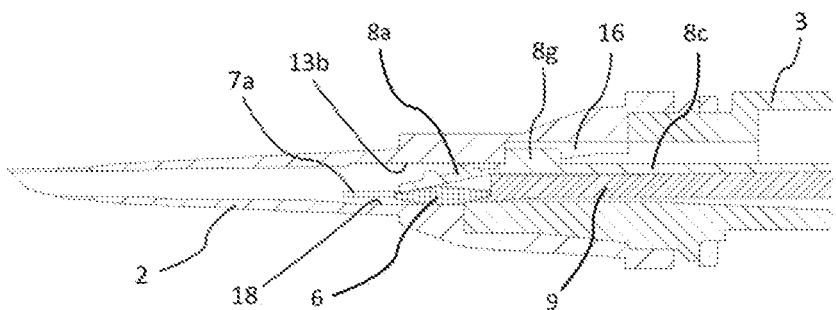
FIG. 7c is an enlarged partial cross-sectional view schematically showing the front end of the intraocular lens implanter according to the first embodiment in a state that the push pin and the pressing plate of the intraocular lens implanter continue to move together so that a retention feature of the pressing plate is retained, and the push pin and the pressing plate are about to separate.
Figure 7D:
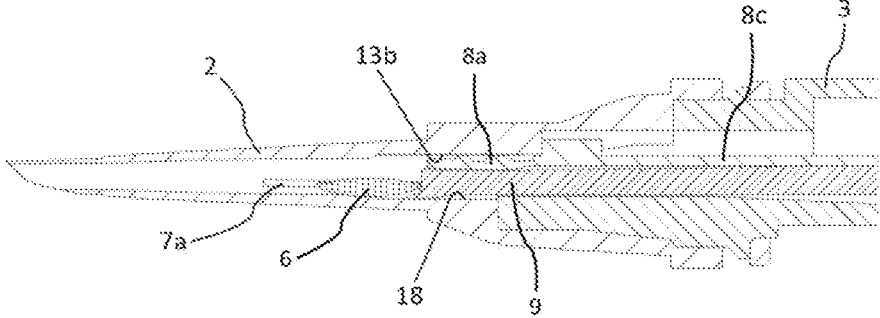
FIG. 7d is an enlarged partial cross-sectional view schematically showing the front end of the intraocular lens implanter according to the first embodiment in a state that the push pin of the intraocular lens implanter continues to move alone so that the head of the push pin is beyond the front end of the movable piece of the pressing plate.
Figure 7E:
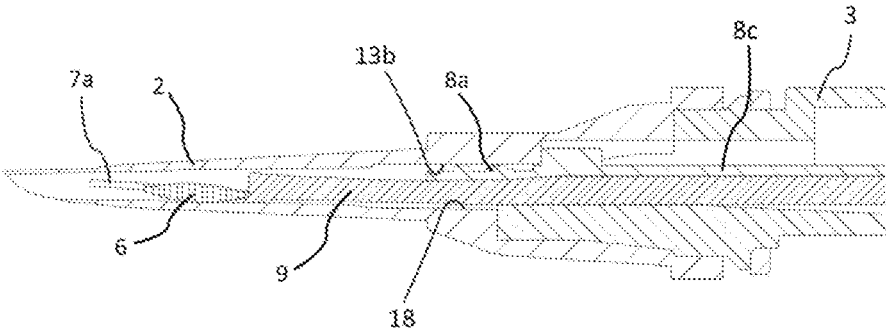
FIG. 7e is an enlarged partial cross-sectional view schematically showing the front end of the intraocular lens implanter according to the first embodiment in a state that the push pin of the intraocular lens implanter continues to move alone so that the intraocular lens is about to reach the mouth of the nozzle portion of the implantation head.
Figure 8A:
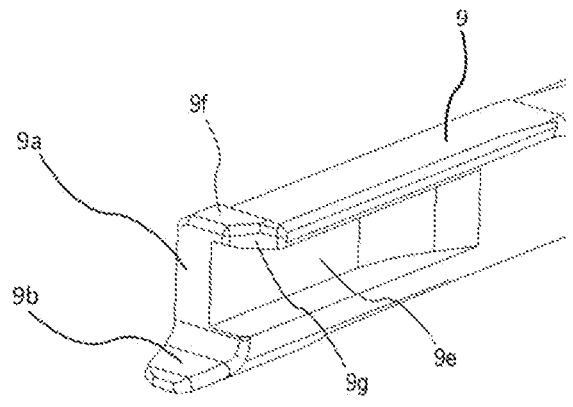
Figure 8B:
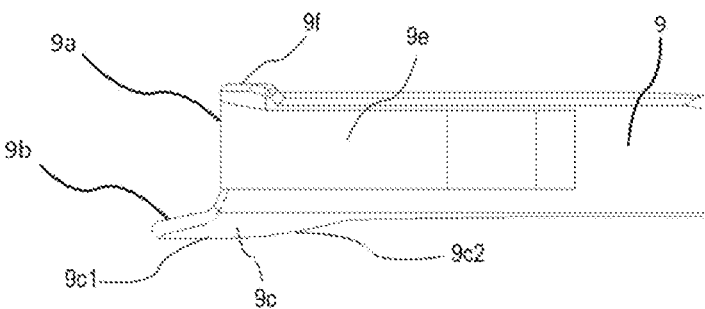
Figure 8C:
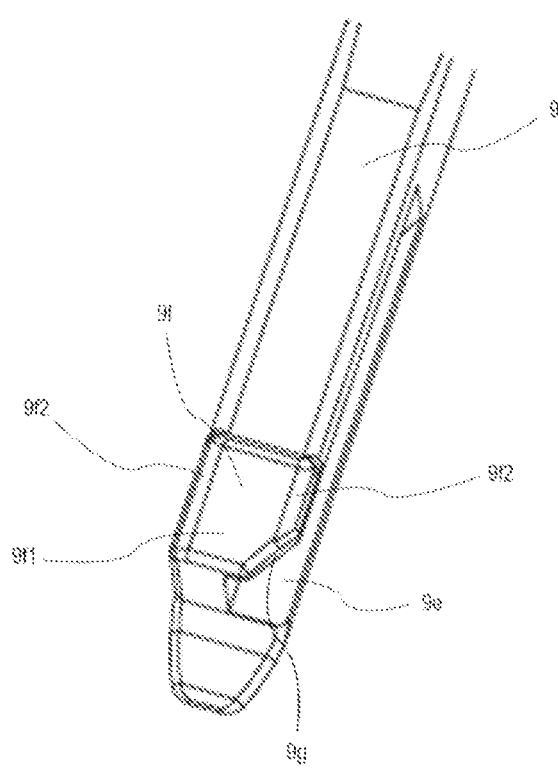
Figure 8D:
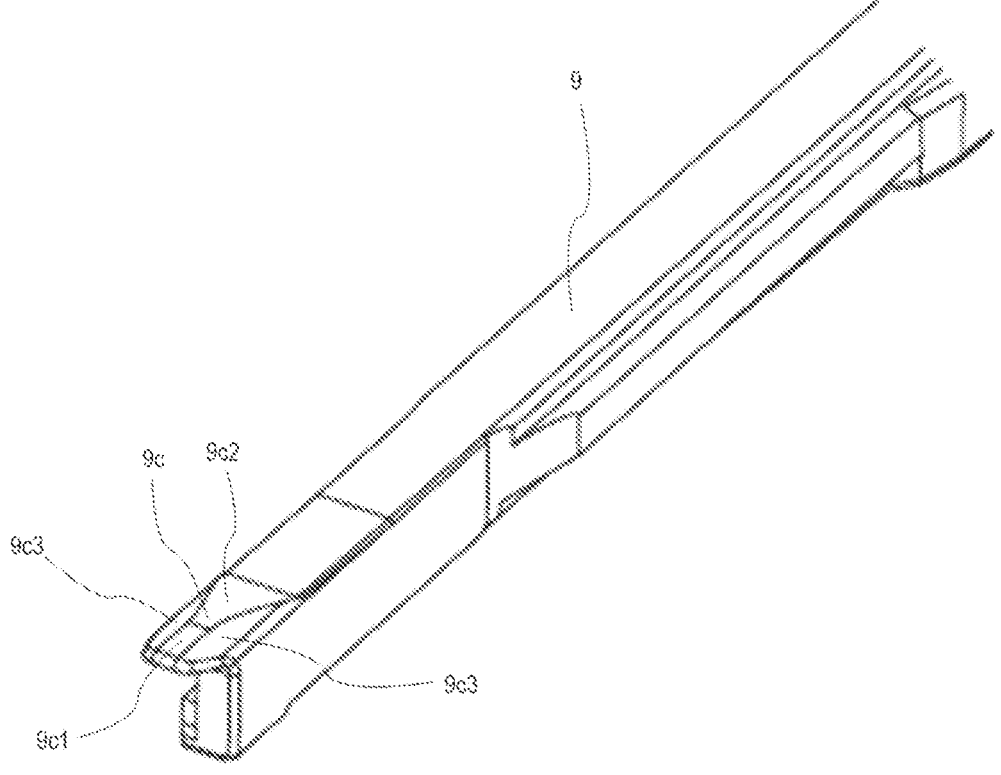
Figure 9:
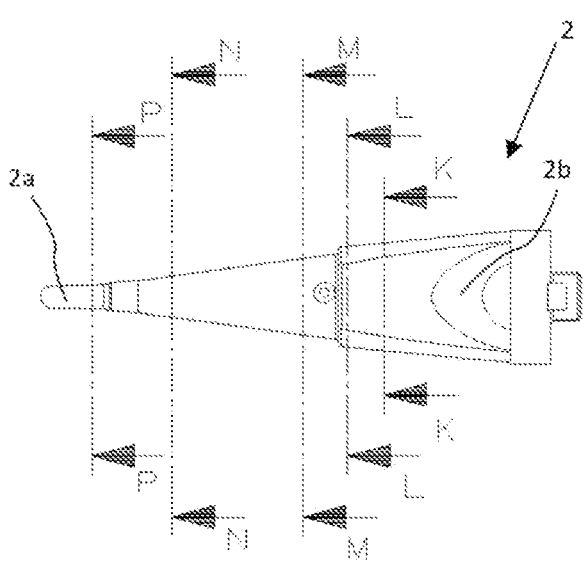
FIG. 9 is a top view schematically showing the implantation head in the first embodiment.
Figure 10A:
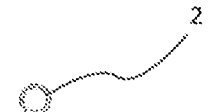
Figure 10B:
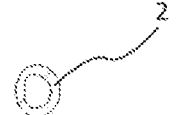
Figure 10C:
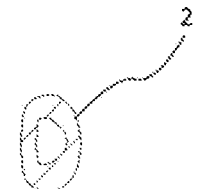
Figure 10D:
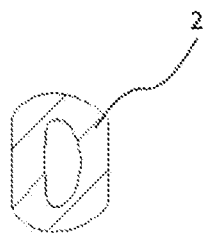
Figure 10E:
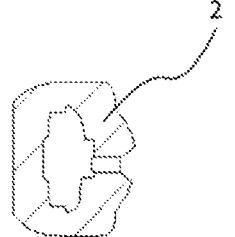
Figure 16:
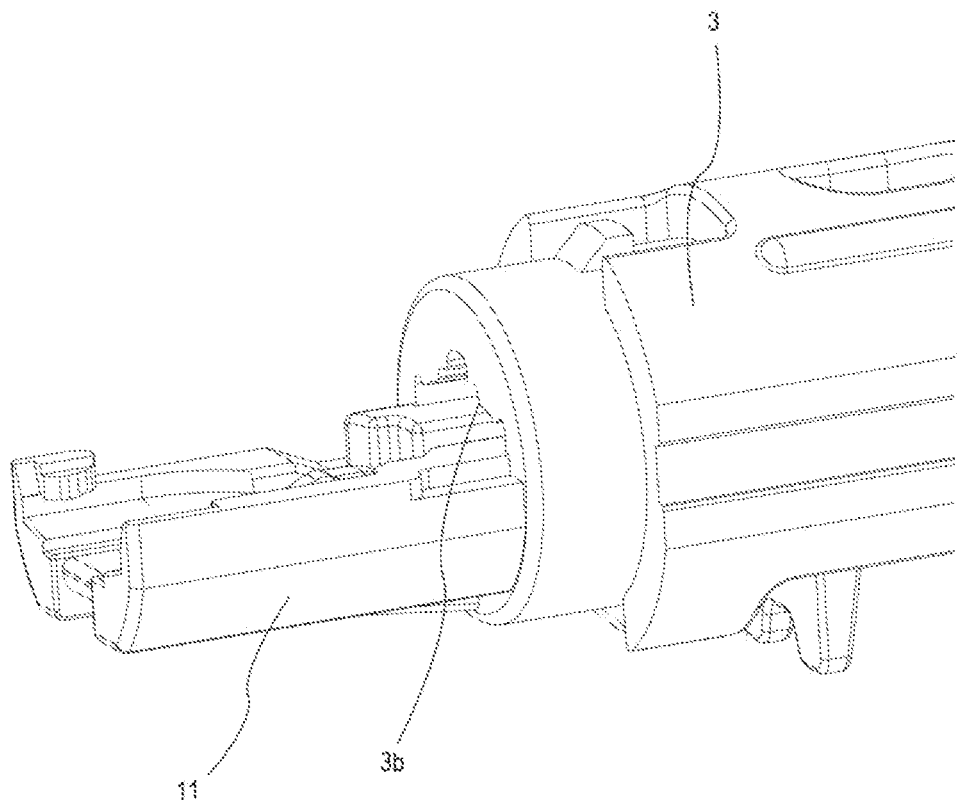
FIG. 16 is an enlarged partial view of the front end of the body of the implanter.

FIG. 1 is a perspective view schematically showing the overall structure of an intraocular lens implanter according to the present embodiment; FIG. 2 is an exploded view schematically showing the structure of the intraocular lens implanter according to the present embodiment; FIG. 3 is an enlarged perspective view schematically showing a head of a push pin; FIG. 4*a* is a perspective view schematically showing a front surface of a pressing plate; FIG. 4*b* is a perspective view schematically showing a rear surface of the pressing plate; FIG. 5*a* is a perspective view schematically showing the assembly of the push pin and the pressing plate; FIG. 5*b* is a partially enlarged perspective view schematically showing the assembly of the push pin and the pressing plate; FIG. 6 is a perspective view schematically illustrating an upper surface of an inner cavity of a transition portion of an implantation head in the first embodiment; FIG. 7*a* is an enlarged partial cross-sectional view schematically showing a front end of the implanter according to the first embodiment when the assembly of the intraocular lens implanter is completed or at the beginning of the injection (initial state); FIG. 7*b* is an enlarged partial cross-sectional view schematically showing the front end of the intraocular lens implanter according to the first embodiment in a state that the push pin and the pressing plate of the implanter move together so that the lens-contacting portion of the head of the push pin is in contact with the side surface of the optic portion of the intraocular lens; FIG. 7*c* is an enlarged partial cross-sectional view schematically showing the front end of the intraocular lens implanter according to the first embodiment in a state that the push pin and the pressing plate of the implanter continue to move together so that retention feature of the pressing plate is retained, and the push pin and the pressing plate are about to separate; FIG. 7*d* is an enlarged partial cross-sectional view schematically showing the front end of the intraocular lens implanter according to the first embodiment in a state that the push pin of the intraocular lens implantation device continues to move alone so that the head of the push pin is beyond the front end of the movable piece of the pressing plate; FIG. 7*e* is an enlarged partial cross-sectional view schematically showing the front end of the intraocular lens implanter according to the first embodiment in a state that the push pin of the implanter continues to move alone so that the intraocular lens is about to reach the mouth of the nozzle portion of the implantation head; FIGS. 8*a* to 8*d* are partially enlarged perspective views schematically showing the head of the push pin according to the first embodiment, wherein FIG. 8*a* is a perspective view seen from the oblique front, FIG. 8*b* is a side view, FIG. 8*c* is a perspective view seen from substantially above, and FIG. 8*d* is a perspective view seen from the lower surface of the push pin; FIG. 9 is a top view schematically showing an implantation head in the first embodiment; FIGS. 10*a*-10*e* are sectional views schematically showing the implantation head in first embodiment in different sections, wherein FIGS. 10*a*-10*e* are sectional views at lines P-P, N-N, M-M, L-L, K-K shown in FIG. 9, respectively; FIG. 16 is an enlarged partial view of the front end of the body of the implanter in FIG. 2.

In the present embodiment, in order to clarify the relative positional relationships of parts of the intraocular lens implanter, directions of actions and the like, front, rear, left, right, up, and down directions are defined, wherein the front-rear direction coincides with the axial direction of the elongated intraocular lens implanter, the left-right direction coincides with the width direction of the intraocular lens implanter, and the up-down direction coincides with the height direction of the intraocular lens implanter. These directions are also indicated in FIG. 1. Furthermore, these defined directions are also applicable in other embodiments.

In addition, the term "optic portion" used in the present disclosure refers to a portion of the intraocular lens having optic portion characteristics so as to perform a main function of adjusting of the diopter of the intraocular lens.

The term "supporting portion" used in the present disclosure refers to a portion connected to the optic portion of the intraocular lens and functioning to support the optic portion and to transfer to the optic portion a contractile force generated by contraction and relaxation of the ciliary muscle.

The term "axis of intraocular lens implanter" used in present disclosure refers to a longitudinal centerline of the elongated intraocular lens implanter.

The term "lower optic portion surface" (corresponding to a first optic portion surface in the present disclosure) used in the present disclosure is relative to the upper optic portion surface (corresponding to a second optic portion surface in the present disclosure) of the optic portion of the intraocular lens, and the lower surface of the optic portion of the intraocular lens preloaded in the implanter refers to the surface of the optic portion which contacts the upper surface of a intraocular lens holder at the front end of the body of the implantation device.

In the following description, the installation positions of the respective members and the positional relationships among the members are the installation positions and the positional relationships in the initial state where the implanter 1 is not in the injection operation, unless otherwise specified.

<Overall Structure>

In the present embodiment, an intraocular lens implanter 1 (may be simply referred to as the implanter 1) is a preloaded type intraocular lens implanter in which an intraocular lens is loaded in advance. As shown in FIGS. 1 and 2, the intraocular lens implanter 1 has an implanter body 3, an implantation head 2 mounted at a front end of the implanter body 3, and a spiral tube 4 mounted at a rear end of the implanter body 3. The front end of the implanter body 3 is provided with an intraocular lens holder 11 on which an intraocular lens 5 is placed in advance. In addition, a push pin 9 is installed inside the implanter body 3, the push pin 9 is arranged behind the intraocular lens 5, and a push rod 10 is installed inside the spiral tube 4. A front end of the push rod 10 is connected to a rear end of the push pin 9.

When the intraocular lens 5 is implanted into a human eye by using the implanter 1, an operator rotates the spiral tube 4, thereby moving the spiral tube 4 forward along the axial direction (the front-rear direction) of the implanter 1 to drive the push rod 10 to move forward, and the push pin 9 is thus driven by the push rod 10 to move forward. The forward-moving push pin 9 pushes the intraocular lens 5 placed in advance on the intraocular lens holder 11 into the implantation head 2, via which the intraocular lens 5 is injected into the eye.

The components of the implantation device 1 will be described below.

<Implanter Body>

As shown in FIG. 2, the implantation device body 3 is substantially cylindrical, and the front end thereof is provided with the lens holder 11 projecting forward from the bottom, and the intraocular lens 5 is placed in advance on the lens holder 11. In the present embodiment, the intraocular lens 5 is made of a hydrophobic soft material. The intraocular lens 5 has a disk-shaped optic portion 6 and a pair of supporting portions, namely, a front supporting portion 7*a* and a rear supporting portion 7*b*, provided on both sides of the optic portion 6. The optic portion 6 has a lower surface (first optic portion surface) and an upper surface (second optic portion surface) facing away from each other. The front supporting portion 7a protrudes forward in an arm shape from the right portion of the optic portion 6, extending obliquely leftward while extending forward to have a substantially L-shape. It has a base end portion 7a1 connected to the optic portion 6 and a front end portion 7a2 as an extended end and a free end, and a space is formed between the front end portion 7a2 and the front edge of the optic portion 6. The rear supporting portion 7b, like the front supporting portion 7a, protrudes rearward in an arm shape from the left portion of the optic portion 6, extending obliquely rightward while extending rearward to have a substantially L-shape. It has a base end portion 7b1 connected to the optic portion 6 and a rear end portion 7b2 as an extended end and a free end, and a space is formed between the rear end portion 7b2 and the rear edge of the optic portion 6.

When the intraocular lens 5 is rolled or folded in a predetermined manner, the front supporting portion 7a and the rear supporting portions 7b are folded upward onto the upper surface of the optic portion 6, respectively, and the left and right edges of the optic portion 6 are rolled upward to wrap the front supporting portion 7a and the rear supporting portions 7b.

The lens holder 11 not only functions to hold the intraocular lens, but also functions to restrict the movement of the intraocular lens in the up-down direction and the left-right direction (see the patent documents 4 and 5 and the like for specific implementation structures, which will not be described in detail herein).

An external thread 3a is provided on an outer peripheral surface of a rear section 12 of the implanter body 3, and the external thread 3a cooperates with an internal thread provided on the spiral tube 4, so that the spiral tube 4 can move in the axial direction of the implanter (the front-rear direction) relative to the implanter body 3 when the spiral tube 4 is rotated.

As shown in FIG. 16, a guide groove 3b is formed on the upper surface of the inner cavity of the implanter body 3, the front end of the guide groove 3b is opened, and a fixed piece 8c of a pressing plate 8, which will be described later, is disposed in the guide groove 3b, and moves forward with the push pin 9 under the guide of the guide groove 3b.
<Spiral Tube (Operating Member) and Push Rod>

As shown in FIG. 1, the spiral tube 4 is coaxially mounted on the rear end of the implanter body 3, and is a member that can be rotated by the operator as described above. A push rod 10 is installed inside the spiral tube 4, a rear end 10b of the push rod 10 is connected to the spiral tube 4 in such a manner that it is rotatable relative to the spiral tube 4 but immovable in the front-rear direction, and a front end 10a of the push rod 10 is connected to a rear end of the push pin 9.
<Push Pin (Injection Member)>

The push pin 9 is installed inside the implanter body 3 in such a manner that it is movable in the front-rear direction, and as described above, the rear end thereof is connected to the front end 10a of the push rod 10. When the push rod 10 moves forward, the push pin 9 is pushed by the push rod 10 to move forward.

As shown in FIGS. 8a and 8b, the front end (head) of the push pin 9 has a lens contacting portion 9a and an extension 9b. The lens contacting portion 9a is a portion that comes into contact with the intraocular lens 5 and pushes the intraocular lens 5 to move, it is formed on the front end surface of the push pin 9, and is configured as a vertical plane extending in the up-down direction. The extension 9b protrudes forward from the lower portion of the lens contacting portion 9a, and the upper surface thereof gradually extends obliquely rearward and upward. The extension 9b is located below the lower surface of the optic portion 6 of the intraocular lens 5 when the push pin 9 pushes the intraocular lens 5 to move. In this way, the reliability of the injection can be ensured, and the push pin 9 can be prevented from moving to the upper surface of the optic portion 6 due to the resistance of the intraocular lens 5 during the injection.

In addition, in particular, in the present embodiment, the extension 9b projects or protrudes forward from the lower portion of the front end surface of the push pin 9, and the portion of the front end surface located above the extension 9b is formed of a single plane (i.e., the lens contacting portion 9a), that is, on the front end surface of the push pin 9, there is no portion protruding forward at other parts (including the upper portion) than the extension 9b, so that it is possible to ensure that the rear supporting portion 7b can be smoothly lifted up without hindrance at the time of folding.

In addition, a groove 9e is formed on the left side surface of the front portion of the push pin 9, the front end of the groove 9e is opened, and the depth of the groove 9e is ⅓ to ½ of the width of the front end portion of the push pin 9, preferably ½ of the width of the push pin. When the push pin 9 pushes the intraocular lens 5 to move, a part (rear part) of the rear supporting portion 7b of the intraocular lens 5 can enter the groove 9e, so that the folded rear supporting portion 7b is always in a stable folded state, and the reliability of the movement of the intraocular lens 5 is further improved. As shown in FIGS. 8a and 8c, a relief portion 9g consisted of a chamfered part is formed at the front end portion of the upper wall of the groove 9e.

As shown in FIG. 8b, the lower surface of the front end portion of the push pin 9 including the extension 9b is formed with a downwardly convex protrusion 9c. As shown in FIG. 8d, the protrusion 9c has a flat portion 9c1, a rear arc transition surface 9c2 located on the rear of the flat portion 9c1 and extending obliquely upward and rearward, and left and right arc transition surfaces 9c3 located on the left and right of the flat portion 9c1 and the rear arc transition surface 9c2 respectively and extending obliquely to the left upper side and the right upper side. The inner cavity of the nozzle portion 2a of the implantation head 2 is generally circular or approximately elliptical in cross section, the cross-sectional dimension of the transition portion 2b of the implantation head 2 gradually decreases toward the nozzle portion 2a, and the lower surface of the inner cavity of the transition portion 2b is generally approximately circular-arc curved surface structure, so by forming the structure of the protrusion 9c, the shape of the lower surface of the front end of the push pin 9 can be matched with the shape of the lower surface of the transition portion 2b of the implantation head 2, so that the push pin 9 is ensured to be kept in contact with the lower surface of the transition portion 2b of the implantation head 2 when passing through the transition portion 2b of the implantation head 2, and meanwhile, when the push pin 9 injects the intraocular lens 5 through the nozzle portion 2a of the implantation head 2, the contact area between the lower surface of the front end of the push pin 9 and the lower surface of the nozzle portion 2a of the implantation head 2 can be ensured to be the maximum, so that the reliability of injection of the intraocular lens 5 can be ensured to the maximum extent.

In addition, as shown in FIGS. 8a and 8b, a protrusion 9f is formed on the upper surface of the front end portion of the push pin 9. As shown in FIG. 8c, the protrusion 9f has a flat portion 9f1, left and right arc transition portions 9f2 located on the left and right of the flat portion 9f1, and a rear arc transition portion located on the rear of the flat portion 9f1. The protrusion 9f functions to reduce the gap between the upper surface of the front end of the push pin 9 and the lower surface of the assembled pressing plate 8, thereby reducing the risk of the rear supporting portion 7b being sandwiched between the upper surface of the front end of the push pin 9 and the lower surface of the pressing plate 8 in the process of folding the rear supporting portion 7b of the intraocular lens 5 onto the upper surface of the optic portion 6 by the push pin 9.

In addition, as shown in FIG. 3, snap-fit recesses 15 are formed on both the left and the right of the rear end of the push pin 9, and the snap-fit recesses 15 engage with snap-fit projections 14 on a pressing plate 8 described later.

<Pressing Plate (Biasing Member)>

As shown in FIG. 2, the implanter 1 may further include the pressing plate 8, which is provided on the implanter body 3 in such a manner that it is movable in the front-rear direction with respect to the implanter body 3. As the portion inside the implanter body 3 that is engaged with the pressing plate 8, a guide groove 3b (mounting groove, FIG. 16) having a shape matching the pressing plate 8 is formed in the implanter body 3, the pressing plate 8 is disposed in the guide groove 3b in such a manner that it is slidable in the front-rear direction along the guide groove 3b, and the pressing plate 8 is also assembled with the push pin 9, which will be described below.

As shown in FIGS. 4a and 4b, the pressing plate 8 is flat as a whole, and is formed of a soft material (for example, a plastic material softer than the push pin 9), and has a movable piece 8a located on the front, a fixed piece 8c located on the rear, and a connecting piece 8b connected between the movable piece 8a and the fixed piece 8c. The fixed piece 8c is movable in the front-rear direction together with the push pin 9 as described later, but the position thereof in the up-down direction is substantially fixed, and the movable piece 8a is movable downward relative to the fixed piece 8c. The connecting piece 8b is provided between the movable piece 8a and the fixed piece 8c, and in the present embodiment, is formed by a thin part thinner than the movable piece 8a and the fixed piece 8c, and the thickness of the connecting piece 8b is preferably 0.2 to 0.4 mm.

In another embodiment, instead of the connecting piece 8b formed by the thin part, a rotating shaft structure may be provided between the movable piece 8a and the fixed piece 8c.

As shown in FIG. 4a, a protrusion 8e is formed on the upper surface of the movable piece 8a. In the present embodiment, there are two projections 8e provided in the front and the rear and having a substantially semi-cylindrical shape whose axial direction coincides with the lateral direction. A stopper protrusion 8g is formed on the upper surface of the fixed piece 8c at a portion close to the connecting piece 8b. The function of the protrusions 8e and the stopper protrusion 8g will be described later.

As shown in FIG. 4b, a pair of snap-fit projections 14 are formed on a rear side portion of the lower surface of the fixed piece 8c of the pressing plate 8. As shown in FIGS. 5a and 5b, the snap-fit projections 14 of the pressing plate 8 are engaged with the snap-fit recesses 15 of the push pin 9, so that the pressing plate 8 and the push pin 9 moves together in the front-rear direction. That is, the pressing plate 8 and the push pin 9 are assembled in such a manner that they can move together in the front-rear direction. After assembly, the pressing plate 8 is positioned above the push pin 9.

As shown in FIG. 4b, a pair of left and right push pin stopper ribs 8d are formed at a front position of the lower surface of the pressing plate 8, and the pair of push pin stopper ribs 8d are arranged at intervals in the left-right direction and slightly offset from each other in the front-rear direction. As shown in FIG. 5a, the pair of push pin stopper ribs 8d are respectively located on the left and right sides of the push pin 9 to limit the position of the push pin 9 in the left-right direction and suppress the eccentricity of the push pin 9 during the movement.

<Implantation Head>

As shown in FIGS. 2 and 9, the implantation head 2 has a nozzle portion 2a for releasing the intraocular lens 5 into the eye, and a transition portion 2b located behind the nozzle portion 2a and having an inner cavity shaped and sized so as to allow the intraocular lens 5 to be folded or rolled and reach the nozzle portion 2a in this state.

The inner cavity of the transition portion 2b has left and right surface features with asymmetric structures. As shown in FIGS. 10a to 10e, the cross-sectional dimension of the inner cavity of the transition portion 2b decreases in a direction from the lens holder to the nozzle portion, so that when the intraocular lens 5 passes through the transition portion 2b, the intraocular lens 5 is deformed at least in such a manner that the lower surface is rolled (or folded) onto the upper surface to achieve a smaller overall dimension. The shapes of the transition portion 2b of the implantation head 2 at various cross-sections from the front to the rear are shown in FIGS. 10a-10e, from which it can be seen that the cross-sectional dimension of the transition portion of the implantation head decreases from the rear to the front. Further, the settings of the shape and size of the transition portion 2b that is capable of causing the intraocular lens 5 (the optic portion 6) to undergo folding deformation from bottom to top have been disclosed in many cases in the prior art (for example, patent documents 1 to 6 described above), and will not be described further herein.

As shown in FIGS. 7a-7e, the upper surface of the inner cavity of the transition portion 2b has a guide portion 13. The guide portion 13 has a shape approaching the central axis of the implanter (the movement route of the push pin 9) from the rear to the front, and has a first slope portion 13a and a second slope portion 13b. The inclination angle of the second slope portion 13b is small, and the first slope portion 13a is connected to and disposed behind the second slope portion 13b. The movable piece 8a of the pressing plate 8 can be pressed down by the first slope portion 13a and the second slope portion 13b to fold downward (produce downward displacement), so that a downward force is applied to the push pin 9.

As shown in FIG. 6, a guide groove 16 extending from the first slope portion 13a to the second slope portion 13b is formed on the guide portion 13 (the upper surface of the inner cavity of the transition portion 2b), and the guide groove 16 is accessible to the stopper protrusion 8g (FIG. 4a) on the fixed piece 8c of the pressing plate 8, thereby guiding the movement of the pressing plate 8 in the front-rear direction. When the stopper protrusion 8g moves to the end (the front end) of the guide groove 16 in the guide groove 16, the stopper protrusion 8g is stopped by the end surface (the front end surface) of the guide groove 16, and the stopper protrusion 8g cannot thus continue to move forward and the pressing plate 8 is stopped. When the push pin 9 moves forward further, the engagement between the push pin 9 and the pressing plate 8 (the engagement between the snap-fit projections 14 and the snap-fit recesses 15) is released, and the push pin 9 moves forward alone and no longer drives the pressing plate to move together.

The structure of the present embodiment will be described in more detail below in conjunction with the injection method and the injection operation.

<Injection Method and Injection Operation>

FIGS. 7a to 7e show an initial state before the injection operation is performed and respective states when the push pin 9 pushes the intraocular lens 5 to the vicinity of the nozzle portion 2a through the injection operation. In addition, the rear supporting portion 7b of the intraocular lens 5 is omitted in FIGS. 7a to 7e for simplicity of drawing, and the intraocular lens 5 is in the same state in FIGS. 7a to 7e, but in fact the intraocular lens is continuously folded in this process until it is folded to the greatest extent. The process of folding or rolling the intraocular lens 5 is disclosed in the prior art, for example, in the above-mentioned patent documents 1 to 5, and will not be described in detail herein.

①Stage 1: Initial State

As shown in FIG. 7a, in the initial state, the intraocular lens 5 is preloaded on the lens holder 11, and the push pin 9 is positioned behind the intraocular lens 5 at a position substantially contacting the rear supporting portion 7b (not shown) of the intraocular lens 5. The movable piece 8a of the pressing plate 8 projects forward relative to the front end portion of the push pin 9, and contacts the first slope portion 13a on the upper surface of the transition portion 2b of the implantation head 2, so that it is pressed down by the first slope portion 13a to be slightly folded down (produce downward displacement). Thus, a downward force is applied to the push pin 9 through the fixed piece 8c, so that the lower surface of the head, i.e., the front end portion (including the extension 9b), of the push pin 9 is in contact with the bottom surface (upper surface) of the lens holder 11 (in other embodiment(s), a slight clearance can be left, the same below).

②Stage 2

Thereafter, as shown in FIG. 7b, the operator rotates the spiral tube 4 to move the push pin 9 forward so as to start the injection operation. The push pin 9 moves forward to a position where the front end surface thereof, i.e., the lens contacting portion 9a, contacts the rear edge of the optic portion 6 of the intraocular lens 5, and at this time, the optic portion 6 of the intraocular lens 5 is held on the lens holder 11 without moving. Further, although not shown, the rear supporting portion 7b of the intraocular lens 5 is pushed by the push pin 9 to deform, and thus moves onto the upper surface (the second optic portion surface) of the optic portion 6.

In addition, since the pressing plate 8 is engaged with the push pin 9 as described above, the pressing plate 8 moves forward as the push pin 9 moves forward. On the one hand, the stopper protrusion 8g on the upper surface of the fixed piece 8c enters the guide groove 16 on the upper surface of the transition portion 2b of the implantation head 2, so that its movement is guided by the guide groove 16, and the eccentricity in the left-right direction is thus suppressed. On the other hand, under the guidance of the first slope portion 13a on the upper surface of the transition portion 2b of the implantation head 2, the movable piece 8a of the pressing plate 8, is further folded down relative to the fixed piece 8c (i.e., the movable piece 8a is gradually pushed down by the first slope portion 13a) while moving forward. In this way, the movable piece 8a applies a downward force to the push pin 9 via the fixed piece 8c, so that at least the lower surface of the front end of the push pin 9 is held in contact with the bottom surface of the lens holder 11.

In addition, in this state, the downwardly inclined front end portion of the movable piece 8a is pressed against the upper surface (the second optic portion surface) of the optic portion 6 of the intraocular lens 5, so that a gap between the lower surface (the first optic portion surface) of the optic portion 6 and the bottom surface (the upper surface) of the lens holder 11 can be reduced, and even the gap is reduced to zero so as to be in a state of contact motion.

③Stage 3

Next, as shown in FIG. 7c, the push pin 9 further moves forward from the state shown in FIG. 7b and drives the pressing plate 8 to further move forward, so that the stopper protrusion 8g on the fixed piece 8c of the pressing plate 8 moves to the end (the front end) of the guide groove 16 and is restricted by the front end surface of the guide groove 16, which makes the pressing plate 8 reach a restricted state and be stopped. In this state, the movable piece 8a is completely moved to the position of the second slope portion 13b on the upper surface of the implantation head 2 (the position coinciding with the second slope portion 13b), in a state where its front end is inclined downward and is held pressed against the upper surface of the optic portion 6 of the intraocular lens 5, so that the gap between the lower surface of the optic portion 6 and the bottom surface (the upper surface) of the lens holder 11 can be reduced, and even the gap is reduced to zero so as to be in a state of contact motion.

In addition, in this state, the intraocular lens 5 has been substantially detached from the lens holder 11, the push pin 9 is about to reach the position of the inner cavity (the lower surface 18) of the implantation head 2 and still is at the position of the lens holder 11, and the lower surface of the front end of the push pin keeps in contact with the bottom surface (upper surface) of the lens holder 11 under the action of the downward force applied thereto by the movable piece 8a of the pressing plate 8.

In addition, although not shown, in the process that the intraocular lens 5 further moves forward from the state shown in FIG. 7b to move in the inner cavity of the transition portion 2b of the implantation head 2, the left and right edges of the optic portion 6 of the intraocular lens 5 are deformed by rolling (or folding) from the bottom to the top (from the bottom surface (the first optic portion surface) side to the top surface (the second optic portion surface) side) under the effect of the shape and size of the inner cavity of the transition portion 2b.

④Stage 4

Thereafter, as shown in FIG. 7d, the push pin 9 continuously performs the injection operation from the state shown in FIG. 7c to move forward. As described above, since the pressing plate 8 is stopped, the push pin 9 is out of engagement with the pressing plate 8 (the engagement of the snap-fit protrusions 14 and the snap-fit recesses 15) and moves forward alone, and thus can gradually come into a state of being overlapped with the movable piece 8a of the pressing plate 8. In this process, the push pin 9 pushes the movable piece 8a from the bottom to top, so that the movable piece 8a abuts against the second slope portion 13b on the upper surface of the inner cavity of the transition portion 2b of the implantation head 2. In this way, the movable piece 8a in turn applies a downward force to the push pin 9, so that the push pin 9 performs the injection operation in a state that at least the lower surface of the front end portion of the push pin 9 is kept in contact with the lower surface 18 of the inner cavity of the transition portion 2b.

⑤ Stage 5

Thereafter, the push pin 9 continues to move forward from the state shown in FIG. 7d, and pushes the intraocular lens 5 (the optic portion 6) to a position close to the nozzle portion 2a as shown in FIG. 7e. In the process, the movable piece 8a, which is pushed by the push pin 9 to abut against the second slope portion 13b and is sandwiched between the push pin 9 and the second slope portion 13b, maintains a state where it applies a downward force to the push pin 9, so that the push pin 9 performs the injection operation in a state where at least the lower surface of the front end portion thereof is kept in contact with the lower surface 18 of the inner cavity of the transition portion 2b.

Then, the push pin 9 continues to move forward from the state shown in FIG. 7e until the intraocular lens 5 is pushed out from the nozzle portion 2a and released into the human eye, thereby completing the injection operation. As shown in FIG. 7e, in the state shown in FIG. 7e, the upper surface of the front-end of the push pin 9 comes close to a state of contacting the upper surface of the inner cavity of the implantation head 2. Thus, in the process that the push pin 9 further moves forward from the state shown in FIG. 7e, both the upper surface and the lower surface of the front end of the push pin 9 are in contact with the surface of the inner cavity of the implantation head 2.

Effects of the Present Embodiment

In the present embodiment, since the intraocular lens 5 is deformed by rolling or folding from the bottom to the top (at least the left and right edges of the optic portion 6 are rolled or folded upward, and the supporting portions are rolled or folded upward), and the pressing plate 8 applies a downward force to the push pin 9, at least the front end of the push pin 9 can be kept in a bottom-supporting movement state as much as possible, so that the operational reliability of the push pin 9 is improved, and the operational reliability of rolling or folding of the intraocular lens in the expected direction is further improved. The pressing plate 8 constitutes a "biasing means" for applying a force to the push pin 9 as an injection member in the present disclosure.

In addition, in the present embodiment, the movable piece 8a is provided on its upper surface with the protrusions 8e so as to be in contact with the first slope portion 13a of the transition portion 2b of the implantation head 2 during the injection, so that the movable piece 8a is subjected a force to easily fold back toward the lower surface of the transition portion 2b while moving, thereby applying a force downward toward the lower surface of the transition portion 2b to the upper surface of the optic portion 6 of the intraocular lens 5 and/or the upper surface of the push pin 9.

In addition, in the present embodiment, the head portion (the front end portion) of the push pin 9 is provided with lens contacting portion 9a and the extension 9b, which can further increase the reliability of the injection operation and avoid the risk that the push pin 9 separates from the side surface edge of the optic portion 6 and moves to the upper surface of the optic portion 6 because the optic portion 6 of the intraocular lens 5 is subjected frictional resistance during the injection. Meanwhile, the lens contacting portion 9a of the push pin 9 is a plane which is approximately vertical to the axis of the implanter, and because the rear supporting portion 7b of the intraocular lens can generate certain upward movement in the process that the rear supporting portion 7b completes the action of folding onto the upper surface of the optic portion 6, and the lens contacting portion 9a of the push pin 9 formed by the plane ensures that the rear supporting portion 7b is not restricted and limited in a predictable movement range in the process of folding upward, the folding of the rear supporting portion 7b can be realized in a more reliable way.

By adopting the present embodiment, the preloaded type intraocular lens implanter can complete the implantation operation of the intraocular lens simply by a single injection operation.

When the intraocular lens implanter is assembled but the injection operation is not yet performed (FIG. 7a), the lower surface of the extension 9b of the push pin 9 is in contact with the bottom surface (the upper surface) of the lens holder 11 of the implanter body 3. Meanwhile, under the combined action of the size of the lens holder 11 and the size of the intraocular lens 5, the lowest point of the lower surface of the optic portion 6 of the intraocular lens 5 placed on the lens holder 11 is in contact with the upper surface of the lens holder 11 or has controllable gap range with the upper surface of the lens holder 11.

In the stage from the initial state of the intraocular lens implanter 1 to the state where the push pin 9 moves forward to contact with the side edge of the optic portion 6 of the intraocular lens 5 (the stage from FIG. 7a to FIG. 7b), the push pin 9 and the pressing plate 8 move together; meanwhile, in the process of this movement, under the combined action of the front end (the front end of the guide groove 3b) of the implanter body 3, the size of the lens holder 11, the size of the intraocular lens 5, the size of the front end portion (the head portion) of the push pin 9, and the size of the pressing plate 8, the lower surface of the extension 9b of the push pin 9 and the upper surface of the lens holder 11 are always in a contact motion state; and the pressing plate 8 is located above the push pin 9 and the movable piece 8a of the pressing plate 8 protrudes from the lens contacting portion 9a of the push pin 9 after the pressing plate 8 and the push pin 9 are assembled, so when the lens contacting portion 9a of the push pin 9 is in contact with the side edge of the optic portion 6 of the intraocular lens 5, the movable piece 8a of the pressing plate 8 is positioned above the upper surface of the optic portion 6 of the intraocular lens 5; during the integral movement of the pressing plate 8 and the push pin 9, the upper surface of the movable piece 8a of the pressing plate 8 or the protrusions 8e on the upper surface of the movable piece 8 comes into contact with the first slope portion 13a on the upper surface of the transition portion 2b of the implantation head 2, and the movable piece 8a of the pressing plate 8 is folded toward the lower surface of the transition portion 2b (producing downward displacement relative to the fixed piece 8c) under the action of the first slope portion 13a.

Thereafter, when the lens contacting portion 9a of the push pin 9 and the side edge of the optic portion 6 are in a contact state, the lower surface of the movable piece 8a of the pressing plate 8 and the upper surface of the optic portion 6 of the intraocular lens 5 are in contact with each other or come into a state having only a certain controllable gap. At this time, because the intraocular lens 5 at the lens holder 11 of the implanter body 3 is not pushed by the push pin 9, the lowest point of the lower surface of the optic portion 6 of the intraocular lens 5 placed on the lens holder 11 and the upper surface of the lens holder 11 are in contact with each other or come into a state having a controllable gap range under the combined action of the size of the lens holder 11 and the size of the intraocular lens 5. Meanwhile, under the combined action of the size of the lens holder 11, the size of the intraocular lens 5, the size of the extension 9b of the push pin 9 and the size of the fixed piece 8c of the pressing plate 8, when the lens contacting portion 9a of the push pin 9 is contacted with the side edge of the optic portion 6, the extension 9b of the push pin 9 is just below the lower surface of the optic portion 6 of the intraocular lens 5, and the lower surface of the extension 9b of the push pin 9 is still in contact with the upper surface of the lens holder 11.

Thereafter, in the stage from the state where the lens contacting portion 9a at the front end of the push pin 9 is in contact with the side edge of the optic portion 6 of the intraocular lens 5 to the state where the pressing plate 8 is stopped after the push pin 9 and the pressing plate 8 has moved together for a set distance (the stage from FIG. 7b to FIG. 7c), the push pin 9 pushes the intraocular lens 5 away from the lens holder 11 so that most of the optic portion 6 of the intraocular lens 5 enters the transition portion 2b of the implantation head 2. During this injection, the pressing plate 8 and the push pin 9 still move together, the movable piece 8a at the front end of the pressing plate 8 will continue to fold toward the lower surface of the transition portion 2b under the action of the first slope portion 13a on the upper surface of the transition portion 2b of the implantation head 2. At this time, if the lower surface of the movable piece 8a contacts with the upper surface of the optic portion 6 of the intraocular lens 5, the continued folding of the movable piece 8a will apply a force downward toward the lower surface of the transition portion 2b to the upper surface of the optic portion 6 of the intraocular lens 5, so that the gap between the lower surface of the intraocular lens 5 and the lower surface of the transition portion 2b of the implantation head 2 is reduced or even can be reduced to zero, and the lower surface of the optic portion 6 of the intraocular lens 5 and the lower surface of the transition portion 2b of the implantation head 2 are in a contact motion state. At this time, if there is a gap between the lower surface of the movable piece 8a of the pressing plate 8 and the upper surface of the optic portion 6 of the intraocular lens 5, the movable piece 8a continues to fold to first eliminate the gap and then make the lower surface of the movable piece 8a and the upper surface of the optic portion 6 of the intraocular lens 5 in contact with each other, and the continued folding after contact applies a force downward toward the lower surface of the transition portion 2b to the upper surface of the optic portion 6 of the intraocular lens 5, so that the gap between the lower surface of the intraocular lens 5 and the lower surface of the transition portion 2b of the implantation head 2 is reduced or even can be reduced to zero, and the lower surface of the optic portion 6 of the intraocular lens 5 and the lower surface of the transition portion 2b of the implantation head 2 are in a contact motion state. At this movement stage, since the head portion of the push pin is still on the lens holder 11 and does not enter the transition portion 2b of the implantation head 2, the lower surface of the extension 9b at the head portion of the push pin 9 is still kept in contact motion state with the upper surface of the lens holder 11.

In short, in the stage from the start of the injection to the state where the pressing plate 8 is stopped by restriction of the stopper means (the front end surface of the guide groove 16), the intraocular lens 5 is separated from the lens holder 11 under the action of the push pin 9 and moves in the transition portion 2b of the implantation head 2. At this time, under the coordination of the cross section size of the inner cavity of the implantation head 2, the size of the intraocular lens 5, the size of the head portion of the push pin 9 and the size of the pressing plate 8 and under the action of the specially designed upper surface 9 (the first slope portion 13a) of the transition portion 2b, the movable piece 8a of the pressing plate 8 continues to fold towards the lower surface of the transition portion 2 (producing downward displacement), thereby applying a force downward toward the lower surface of the transition portion 2b to the upper surface of the optic portion 6 of the intraocular lens 5 located below the movable piece 8a, so that the gap between the lower surface of the optic portion 6 of the intraocular lens 5 and the lower surface of the transition portion 2b is reduced, or even can be reduced to zero so as to be in a state of contact motion. In addition, at this time, the push pin 9 still maintains the state that the lower surface of the extension 9b and the upper surface of the lens holder 11 are in a state of contact motion. In this way, the operational reliability and operational stability of the folding or rolling of the intraocular lens 5 in the expected direction and the operational reliability and operational stability of the injecting of the intraocular lens 5 by the push pin 9 are ensured in this stage.

Thereafter, in this stage from the state where the pressing plate 8 is stopped to the state where the lens contacting portion 9a at the head portion of the push pin 9 moves to the front end of the movable piece 8a of the pressing plate 8 (the stage from FIG. 7c to FIG. 7d), the pressing plate 8 stops moving under the constraint of the stopper means (the front end surface of the guide groove 16), and as a result of the injection force being continuously applied, the push pin 9 is disengaged from the pressing plate 8 and moves forward alone independently from the pressing plate 8 to complete the injection operation.

In this stage from a state where the push pin 9 is disengaged from the pressing plate 8 to a state where the head portion of the push pin 9 moves to the front end of the movable piece 8a of the pressing plate 8, both the optic portion 6 of the intraocular lens 5 and the head portion of the push pin 5 have moved completely from the lens holder 11 into the transition portion 2b of the implantation head 2 and the optic portion 6 of the intraocular lens 5 and the head portion of the push pin 9 have completely exceeded the movable piece 8a of the pressing plate 8, as described above. When the pressing plate 8 stops movement under the action of the stopper means, the movable piece 8a of the pressing plate 8 has produced downward displacement relative to the fixed piece 8c (at the position of the second slope portion 13b) under the action of the specially designed upper surface of the transition portion 2b of the implantation head 2, and the lower surface of the movable piece 8a has come into contact with the upper surface of the optic portion 6 of the intraocular lens 5 and exerts a force to the intraocular lens 5 which is directed downward toward the lower surface of the inner cavity (inner cavity channel) of the transition portion 2b. When the pressing plate 8 stops movement and the intraocular lens 5 and the push pin 9 continue to move and gradually pass under the movable piece 8a of the pressing plate 8, because the movable piece 8a of the pressing plate 8 maintains the state of producing a downward displacement under the action of the specially designed upper surface (the second slope part 13b) of the transition portion 2b, the movable piece 8a of the pressing plate 8 always applies a force downward toward the lower surface of the transition portion 2b of the implantation head 2 to the intraocular lens 5 and the push pin 9 passing below, thereby ensuring that the lower surface of the optic portion 6 of the intraocular lens 5 and the lower surface of the extension 9b of the push pin 9 are always in a state of contact motion with the lower surface of the transition portion 2b.

Thereafter, in this stage where the intraocular lens 5 and the push pin 9 project from the front end of the movable piece 8a of the pressing plate 8 and continue to move until the intraocular lens 5 is pushed out from the tubular nozzle portion 2*a* of the implantation head 2, the lower surface of the optic portion 6 of the intraocular lens 5 and the lower surface of the transition portion 2*b* are in a state of contact motion when the intraocular lens 5 projects from the front end of the movable piece 8*a* of the pressing plate 8. At this time, the intraocular lens 5 is restricted by the inner cavity of the implantation head 2 and has been in an irreversible expected folding or rolling state, and it is not possible to fold or roll in the opposite direction. Subsequently, under the action of the cross-sectional size of the transition portion 2*b* of the implantation head 2 and the size of the lens, the intraocular lens 5 always keeps the lower surface of the optic portion 6 and the lower surface of the transition portion 2*b* in a state of contact motion until the intraocular lens 5 is pushed out from the tubular nozzle portion 2*a* of the implantation head 2. In the process, the intraocular lens 5 is only further folded or rolled to reduce its own volume under the action of the cross-sectional size of the transition portion 2*b*.

As described above, the head portion of the push pin 9 is subjected to the downward force of the movable piece 8*a* of the pressing plate 8 in the folded state when it protrudes from the front end of the movable piece 8*a* of the pressing plate 8, which keeps the lower surface of the extension 9*b* of the push pin 9 and the lower surface of the transition portion 2*b* of the implantation head 2 in a state of contact motion. In the subsequent process that the push pin 9 continues to perform the injection operation, because the movable piece 8*a* of the pressing plate 8 is still always in the folded state where the downward displacement is produced, the push pin 9 passing through from the lower part of the movable piece 8*a* of the pressing plate 8 is always subjected to a force downward toward the lower surface of the transition portion 2*b*, so that the lower surface of the extension 9*b* of the push pin 9 is always in a state of contact motion with the transition portion 2*b* until the push pin 9 completes the injection operation.

In short, in this stage, under the action of the cross-sectional size of the transition portion 2*b* of the implantation head 2 and the size of the lens, the intraocular lens 5 will always keep the lower surface of the optic portion 6 and the lower surface of the transition portion 2*b* in a state of contact motion and is in the state of further folding in the expected direction. In this stage, under the combined action of the cross-sectional size of the transition portion 2*b* of the implantation head 2, the size of the head portion of the push pin 9, the sizes of the movable piece 8*a* of the pressing plate 8 and the pressing plate 8, and the specially designed upper surface (the second slope 13*b*) of the transition portion 2*b*, the push pin 9 will always subjected to a force towards the lower surface of the transition portion, which is formed due to the downward displacement produced by the movable piece 8*a* of the pressing plate 8, so that the lower surface of the extension 9*b* of the push pin 9 is always in a state of contact motion with the lower surface of the transition portion 2*b*.

In addition to the specially designed upper surface structure of the transition portion 2*b* of the implantation head 2 of the intraocular lens implanter 1 according to the present embodiment, it is not necessary to specially design that the lower surface of the transition portion 2*b* of the implantation head 2 has a slope feature that allows the left and right edges of the lower surface of the intraocular lens 5 to be raised (rolled or folded), which simplifies the structural design of the inner cavity of the transition portion 2*b* of the implantation head 2. Meanwhile, on the premise of ensuring that the lower surface of the intraocular lens 5 and the lower surface of the extension 9*b* of the push pin 9 is in a state of contact motion with the lower base of the transition portion 2*b* of the implantation head 2, the frontend of the push pin 9 is designed with the extension, thereby further avoiding the risk that the lens contacting portion 9*a* at the head portion of the push pin 9 separates from the side edge surface of the optic portion of the intraocular lens 5 and moves to the lower surface of the optic portion 6 of the intraocular lens 5 due to the movement resistance of the intraocular lens 5 in the injection process. In addition, no lifting structure is arranged on the implanter 1 (specifically, the lens holder 11 and the lower surface of the inner cavity of the implanter 1), and the push pin always moves in a bottom-supporting movement state and is not subjected to any resistance, which can simplify the injection operation of the operator and reduce the difficulty of the injection operation.

In the intraocular lens implanter according to the present embodiment, the lower part of the fixed piece 8*c* of pressing plate 8 is equipped with the asymmetric stopper ribs 8*d*, which enable the push pin 9 to be constrained in the process that the push pin 9 and the pressing plate 8 move together, even in the process that the push pin 9 separates from the pressing plate 8 and moves alone for the injection, thereby ensuring that the push pin 9 does not deviate from the position of the center line of the optic portion 6 of the intraocular lens 5 when the intraocular lens 5 is subjected to the injection resistance. The reason why the stopper ribs 8*d* of the fixed piece 8*c* of the pressing piece 8 can function to constrain the push pin 9 is that the pressing piece 8 is also constrained by the relevant stopper means of the implanter body 3 and the implantation head 2 when it moves.

From the above, it can be seen that the intraocular lens implanter 1 according to the present embodiment not only has a simple operation, but also has a great improvement in ensuring the operational reliability and operational stability of the two key actions of implantation of the intraocular lens 5, i.e., the rolling or folding of the intraocular lens 5 in the expected direction and the injection of the intraocular lens 5 via the push pin 9. Meanwhile, the pressing plate 8 is added the stopper ribs 8*d*, which further avoids and reduces the risk that the lens contacting portion 9*a* at the head portion of the push pin 9 deviates from the center position of the optic portion 6 of the intraocular lens 5 because the intraocular lens 5 is subjected to the injection resistance during the injection.

Second Embodiment

The second embodiment of the present disclosure will be described below with reference to FIG. 11. In the description of the present embodiment, the same reference numerals are given to the same components as those of the above-described embodiment, and detailed description thereof is omitted.

Figure 11:
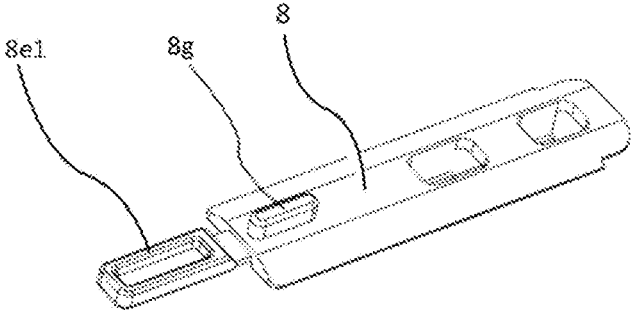
FIG. 11 is a perspective view schematically showing protrusions on the upper surface of a movable piece of the pressing plate in a second embodiment.

FIG. 11 is a perspective view schematically showing a protrusion on the upper surface of the movable piece of the pressing plate in the second embodiment.

This embodiment is different from the above-mentioned first embodiment in that, in the above-mentioned first embodiment, two semi-cylindrical protrusions 8*e* are provided on the upper surface of the movable piece 8*a*, but in the present embodiment, instead of the semi-cylindrical protrusions 8e, an annular protrusion 8e1 extending along the edge of the movable piece 8a is formed.

Third Embodiment

The third embodiment of the present disclosure will be described below with reference to FIG. 12. In the description of the present embodiment, the same reference numerals are given to the same components as those of the above-described embodiment, and detailed description thereof is omitted.

Figure 12:
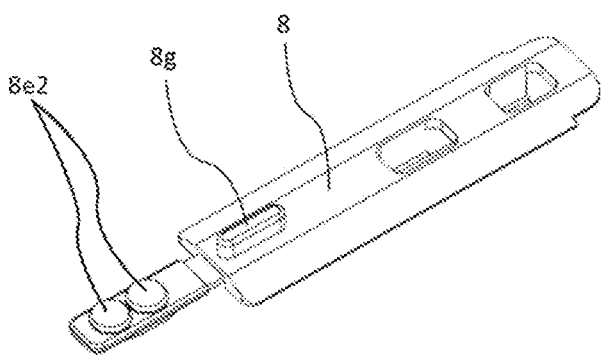
FIG. 12 is a perspective view schematically showing protrusions on the upper surface of the movable piece of the pressing plate in a third embodiment.

FIG. 12 is a perspective view schematically showing a protrusion on the upper surface of the movable piece of the pressing plate in the third embodiment.

This embodiment is different from the above-mentioned first embodiment in that, in the above-mentioned first embodiment, the two semi-cylindrical protrusions 8e are provided on the upper surface of the movable piece 8a, but in the present embodiment, instead of the semi-cylindrical protrusions 8e, a pair of front and rear discoid protrusions 8e2 are formed.

Fourth Embodiment

The fourth embodiment of the present disclosure will be described below with reference to FIG. 13. In the description of the present embodiment, the same reference numerals are given to the same components as those of the above-described embodiment, and detailed description thereof is omitted.

Figure 13:
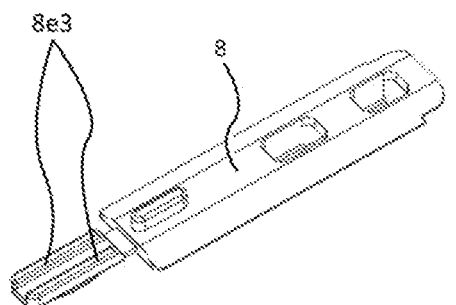
FIG. 13 is a perspective view schematically showing protrusions on the upper surface of the movable piece of the pressing plate in a fourth embodiment.

FIG. 13 is a perspective view schematically showing a protrusion on the upper surface of a movable piece of a pressing plate in the fourth embodiment.

This embodiment is different from the above-mentioned first embodiment in that, in the above-mentioned first embodiment, the two semi-cylindrical protrusions 8e are provided on the upper surface of the movable piece 8a, but in the present embodiment, instead of the semi-cylindrical protrusions 8e, a pair of left and right strip-like protrusions 8e3 parallel to each other are formed.

Fifth Embodiment

The fifth embodiment of the present disclosure will be described with reference to FIG. 14. In the description of the present embodiment, the same reference numerals are given to the same components as those of the above-described embodiment, and detailed description thereof is omitted.

Figure 14:
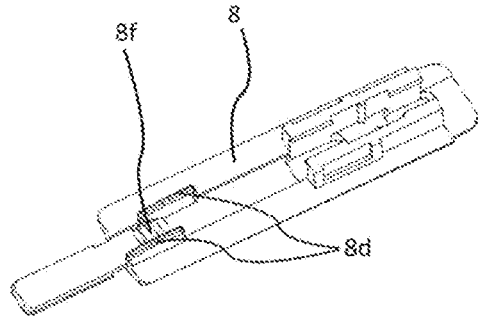
FIG. 14 is a perspective view schematically showing a push pin pressing protrusion on the lower surface of the movable piece of the pressing plate in a fifth embodiment.

FIG. 14 is a perspective view schematically showing a push pin pressing protrusion on the lower surface of the fixed piece of the pressing plate in the fifth embodiment.

As shown in FIG. 14, a push pin pressing protrusion 8f projecting toward a side of the push pin 9 (downward) is formed on the lower surface of the fixed piece 8c of the pressing plate 8, and the push pin pressing protrusion 8f is located at a position close to the front end of the fixed piece 8c and substantially between the pair of left and right push pin stopper ribs 8d. By providing the push pin pressing protrusion 8f, the fixed piece 8c of the pressing plate 8 can apply a downward force to the push pin 9 in a more reliable manner, and the push pin 9 can be kept in the state of bottom-supporting movement. Moreover, providing of the push pin pressing protrusion 8f can reduce the contact area between the pressing plate 8 and the push pin 9 and the movement resistance of the pressing plate 8 to the push pin 9.

Sixth Embodiment

The sixth embodiment of the present disclosure will be described below with reference to FIG. 15. In the description of the present embodiment, the same reference numerals are given to the same components as those of the above-described embodiment, and detailed description thereof is omitted.

Figure 15:
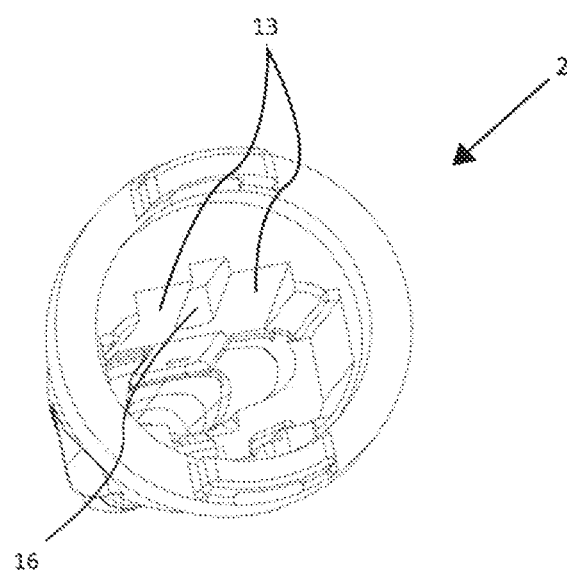
FIG. 15 is a perspective view schematically showing the configuration of the upper surface of the inner cavity of the transition portion of the implantation head in a sixth embodiment.

FIG. 15 is a perspective view schematically showing the configuration of the upper surface of the inner cavity of the transition portion of the implantation head in the sixth embodiment.

This embodiment is different from the above-mentioned first embodiment in that, in the above-mentioned first embodiment, the guide portion 13 is formed of two slope portions 13a and 13b having different inclination angles, but in the present embodiment, the guide portion 13 is formed of a single slope portion. An inclination angle of the slope portion with respect to the central axis of the implanter (the movement route of the push pin 9) is set depending on the size of the movable piece 8a of the pressing plate 8, and may be set in the range of 1.5 to 25°, preferably 2.5 to 11°, more preferably 3.5 to 6.5°.

The above description is only for the purpose of illustrating the preferred embodiments of the present disclosure and should not be regarded as a limitation to the scope of the present disclosure. Any modifications, equivalents, improvements and the like made within the spirit and principle of the present disclosure should fall within the scope of protection of the present disclosure.

Modifications of First to Sixth Embodiments

For example, although in the above embodiments, the preloaded implanter 1 is taken as an example for explanation, the present disclosure is also applicable to a non-preloaded implanter.

In the above embodiments, the biasing means of the present disclosure has been described by taking the pressing plate 8 (the biasing member) as an example, however, the present disclosure is not limited thereto. The biasing member may be any structure capable of applying the aforementioned force to the push pin 9. For example, the shape of the pressing plate 8 is not limited to a plate shape; it is not necessary that the biasing member movable relative to the implantation head 2 is provided, and the biasing member may be fixedly provided on the implantation head 2; or, the pressing plate 8 may not move along with the push pin 9, and may be additionally moved by the operator. In addition, in the above embodiments, the protrusions 8e are provided on the upper surface of the movable piece 8a of the pressing plate 8, however, the protrusions 8e may be omitted. Furthermore, the upper surface of the movable piece 8b may be a plane or a slope with a certain inclination angle according to the shape of the upper surface of the transition portion.

In the above embodiments, the guide portion 13 is formed by a planar slope, but the present disclosure is not limited to this, and the guide portion 13 may also be formed by a curved surface having an inclination tendency. Furthermore, it is also possible to replace the second slope portion 13b of the guide portion 13 with a plane parallel to the movement route of the push pin 9. Further, the upper surface of the inner cavity of the transition portion may be a fixed slope or a movable slope.

Seventh Embodiment

Figure 17:
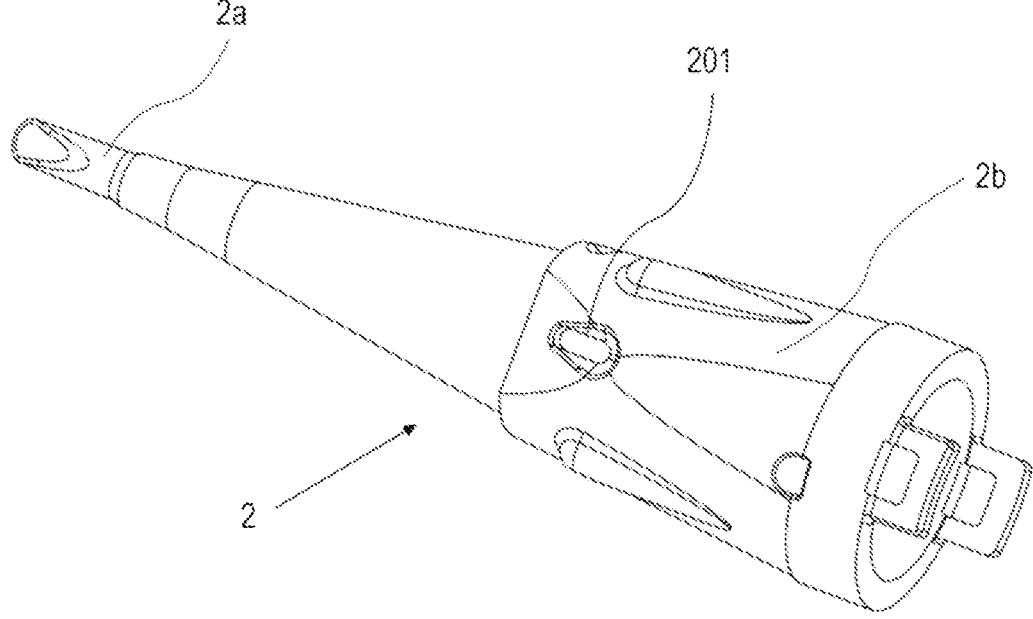
FIG. 17 is a perspective view of the implantation head of a preloaded type intraocular lens implanter according to a seventh embodiment, as seen from the direction of the lower through hole.
Figure 18:
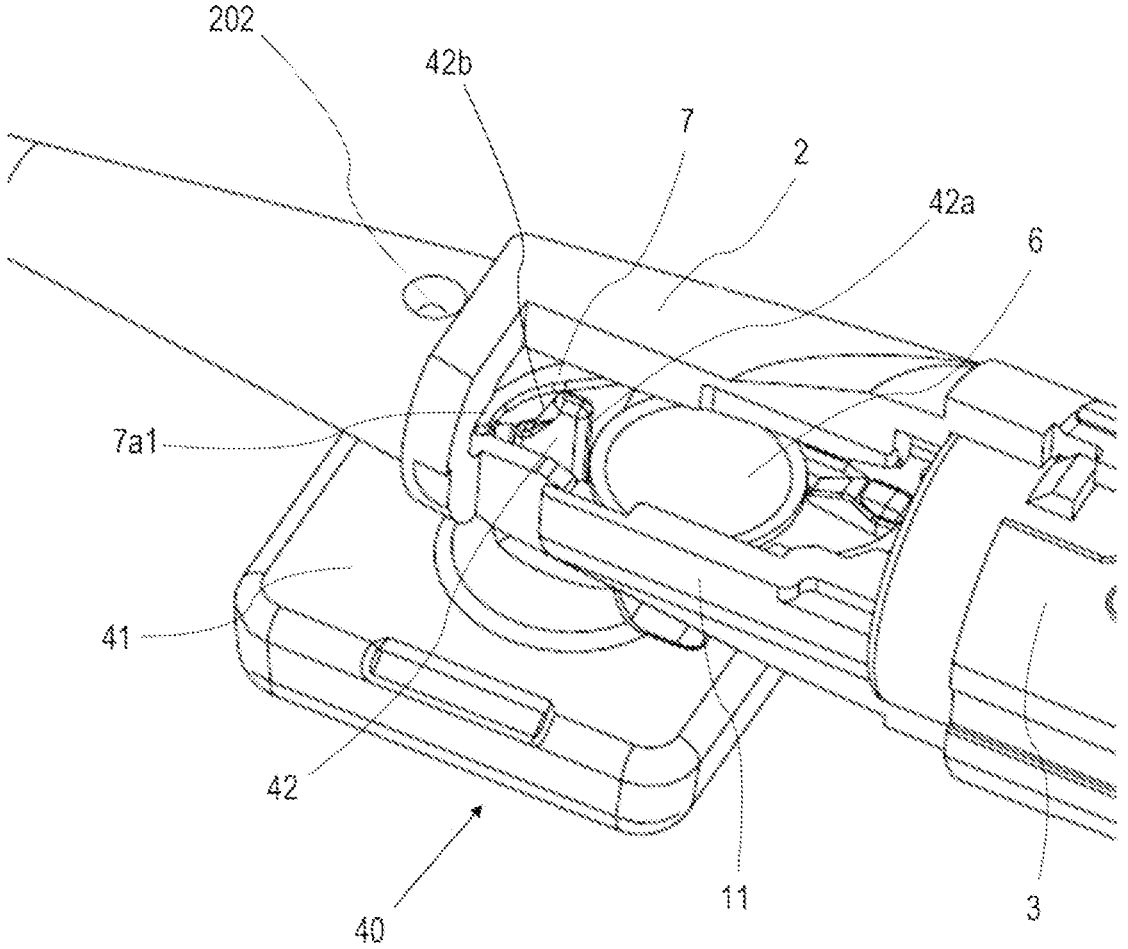
FIG. 18 is an enlarged partial sectional view schematically showing the assembled state of the implantation head of a preloaded type intraocular lens implanter and a retaining mount according to the seventh embodiment.
Figure 19:
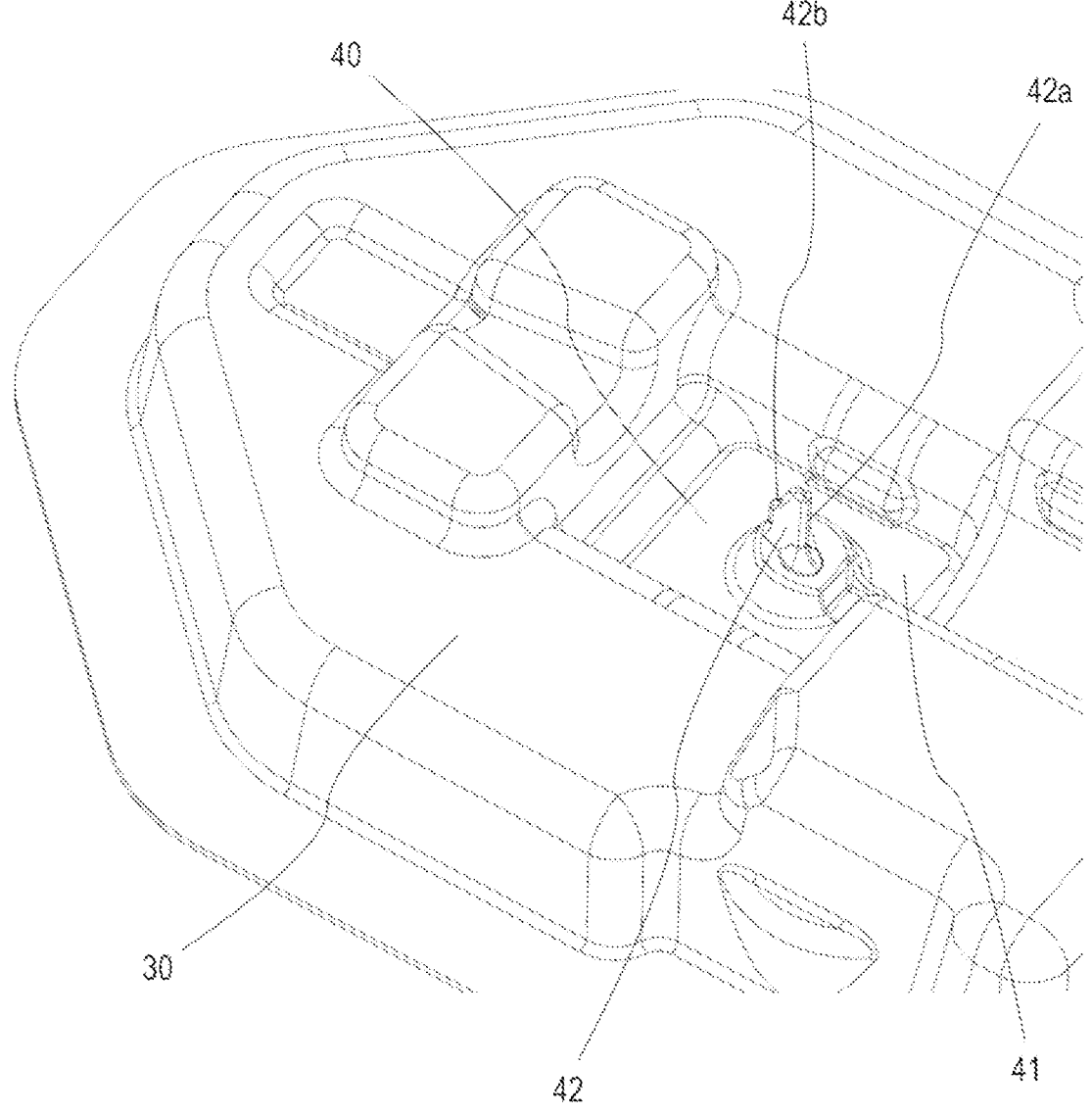
FIG. 19 is an enlarged partial view schematically illustrating the retaining mount and an inner packaging member in an assembly state.
Figure 20:
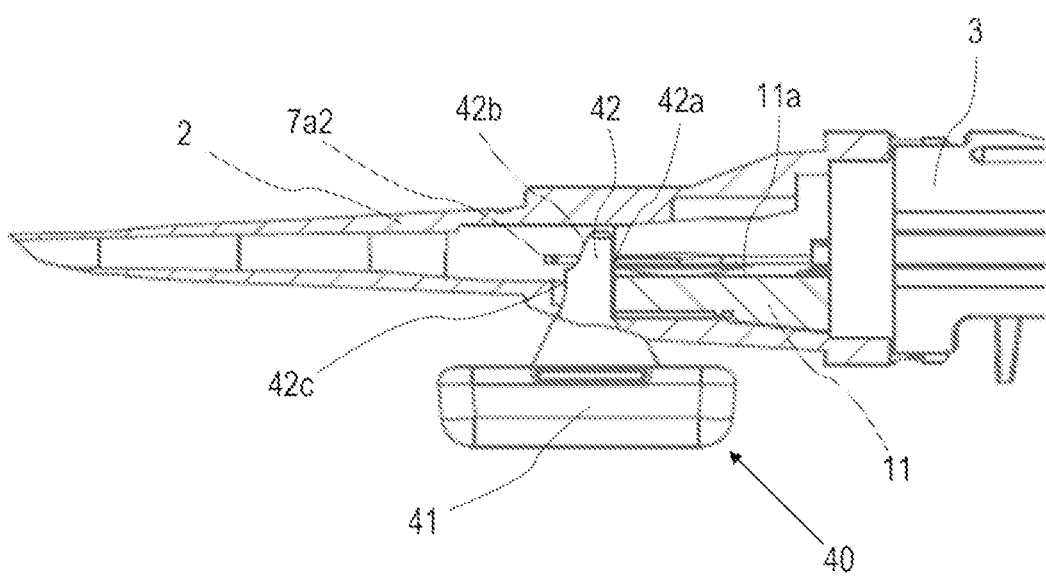
FIG. 20 is an enlarged partial sectional view schematically showing the assembled state of the implantation head of the preloaded type intraocular lens implanter and a retaining mount according to the seventh embodiment.
Figure 21:
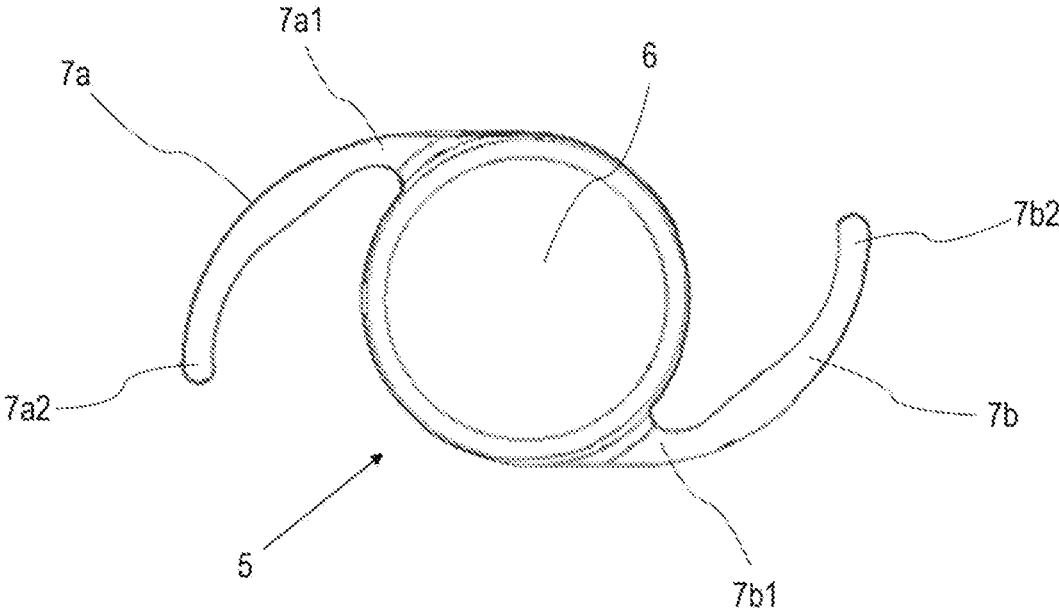
FIG. 21 is a top view of an intraocular lens.

The seventh embodiment of the present disclosure will be described below with reference to FIGS. 17 to 21. FIG. 17 is a perspective view of the implantation head of a preloaded type intraocular lens implanter according to the seventh embodiment, as seen from the direction of the lower through hole; FIG. 18 is an enlarged partial sectional view schematically showing the assembly of the implantation head of the preloaded type intraocular lens implanter and a retaining mount according to the seventh embodiment; FIG. 19 is an enlarged partial view schematically illustrating the retaining mount and an inner packing in an assembly state FIG. 20 is an enlarged partial sectional view schematically showing the assembly of the implantation head of the preloaded type intraocular lens implanter and the retaining mount according to the seventh embodiment; and FIG. 21 is a top view of the intraocular lens.

The present embodiment relates to a preloaded type intraocular lens implantation device. In the present embodiment, the preloaded intraocular lens implantation device includes the intraocular lens implanter 1 as described above, the intraocular lens 5 preloaded in the intraocular lens implanter 1, an inner packaging member 30, and a retaining mount 40. In the following description, the same reference numerals are given to the same components as those of the above-described embodiments, and detailed description thereof will be omitted.

As shown in FIG. 17, the implantation head 2, specifically, the lower part of the transition portion 2b is provided with a pin hole 201, and the position of the pin hole 201 in the front-rear direction is set to be approximately between the front end portion of the front supporting portion 7a of the intraocular lens 5 located on the lens holder 11 and the front edge of the optic portion 6. A retaining pin 42 of the retaining mount 40 described later is inserted in the pin hole 201.

In addition, as shown in FIG. 18, the implantation head 2, specifically an upper portion of the transition portion 2b is provided with a filling port 202. The filling port 202 is constituted by a through hole penetrating the inside and the outside of the implantation head 2. Before the injection operation is performed, viscoelastic agent is filled into the implantation head 2 through the filling port 202. Further, in the present embodiment, the position of the filling port 202 in the front-rear direction is set to be located in front of (upper front of) the front end portion 7a2 of the front supporting portion 7a of the intraocular lens 5.

<Inner Packaging Member>

The implanter 1 is usually packed in the inner packaging member 30 during transport and handling and until before surgery (injection of the intraocular lens) is performed. A portion of the inner packaging member 30 that cooperates with the implantation head 2 of the implanter 1 is shown in FIG. 19. A more specific structure thereof is disclosed in detail in CN104127264A, for example, and thus will not be described in further detail herein.

<Retaining Mount>

As shown in FIG. 19, the retaining mount 40 is installed on the inner packaging member 30. In the present embodiment, the retaining mount 40 and the inner packaging member 30 are manufactured by different methods, that is, the retaining mount 40 is formed into an injection molded part by injection molding, and the inner packaging member 30 is formed into a suction molded part by suction molding. In this way, the retaining mount 40 having a complicated shape can be easily molded, as compared with the case where the retaining mount 40 is integrally formed on the inner packaging member 30.

Referring to FIGS. 18 and 20, the retaining mount 40 includes a holder 41 and a retaining pin 42. The holder 41 is formed as a substantially square base and is engaged with the inner packaging member 30. The retaining pin 42 is provided upright on the upper surface of the holder 41, and the holder 41 and the retaining pin 42 are integrally formed.

Referring to FIGS. 18 and 20, in a state where the implanter 1 is packed in the inner packaging member 30, the retaining pin 42 of the retaining mount 40 is inserted into the implantation head 2 through the pin hole 201 of the implantation head 2 and located in a space between the front end portion 7a2 (a free end portion) of the front supporting portion 7a of the intraocular lens 5 and the front edge of the optic portion 6. In this way, the movement of the optic portion 6 and further the intraocular lens can be blocked by the retaining pin 42 to form a limit thereto.

As shown in FIG. 18-6, a rear surface 42a of the retaining pin 42 facing the optic portion 6 of the intraocular lens 5 is constituted by a straight vertical surface as viewed in the left-right direction, which serves as a stopper surface that blocks forward movement of the optic portion 6. The front surface of the retaining pin 42 is constituted by a vertical surface 42c on the lower side and a guide surface 42b on the upper side, the vertical surface 42c being straight as viewed in the left-right direction, and the guide surface 42b being formed at least in a portion of the front surface of the retaining pin 42 whose height is above a lower bottom surface 11a of the intraocular lens holder 11. In the present embodiment, the guide surface is constituted by a straight slope extending obliquely upward and rearward.

Further, when viewed in the left-right direction, the retaining pin 42 (specifically, a maximum width portion of the retaining pin 42 in the front-rear direction) is set to have a width in the front-rear direction substantially the same as the distance between the front end portion 7a2 (free end portion) of the front supporting portion 7a of the optic portion 6 and the front edge of the optic portion 6, so that the front supporting portion 7a of the intraocular lens can be better restrained in an ideal state.

Regarding the specific configuration of the guide surface 42b, it is formed by a straight slope in the present embodiment. Specifically, as shown in FIGS. 18 to 20, the slope for constituting the guide surface 42b is formed over a part of the length in the front-rear direction of the retaining pin 42 from the front to the rear. However, it is not limited thereto, and the slope for constituting the guide surface 42b may also be formed over the entire length in the front-rear direction of the retaining pin 42 from the front to the rear.

Effect of Seventh Embodiment

The effects of the present embodiment will be described below in conjunction with the methods of assembling and using the preloaded type intraocular lens implantation device.

With the preloaded type intraocular lens implantation device of the present embodiment, during assembly, the retaining mount 40 is first assembled on the inner packaging member 30, then the preloaded type intraocular lens implanter 1 is assembled on the inner packaging member 30, and the retaining pin 42 of the retaining mount 40 is just inserted into the pin hole 201 of the implantation head 2 of the assembled implanter 1, so that the retaining pin 42 of the retaining mount 40 is positioned in the space between the front edge of the optic portion 6 of the intraocular lens 5 in the implanter 1 and the front end portion 7a2 of the front supporting portion 7a. In this way, the rear surface 42a of the retaining pin 42 functions to retain the movement of the intraocular lens 5 towards the nozzle portion 2*a* of the implantation head 2.

When the intraocular lens is implanted, the viscoelastic agent is first filled through the filling port 202 of the implantation head 2, and then the preloaded type intraocular lens implanter 1 is removed vertically from the inner packaging member 30, and the injection member 9 of the implantation device 1 is operated to complete the injection operation of the lens. Since the filling port 202 for the viscoelastic agent is located in front of the front supporting portion 7*a* of the intraocular lens 5, it is possible that the front supporting portion 7*a* is pushed back by the flow of the filled viscoelastic agent and folded in contact with the front surface of the retaining pin 42, and since the portion of the front surface of the retaining pin 42 whose height is above the lower bottom surface 11*a* of the intraocular lens holder 11 is a slope (the guide surface 42*b*) extending obliquely upward and rearward, the front supporting portion 7*a* of the intraocular lens 5 will slide upward along this slope, making the front supporting portion 7*a* higher than the upper surface of the optic portion 6 of the intraocular lens 5. In this state, when the implanter 1 is removed from the inner packaging member 30, since the inner cavity channel of the implantation head 2 has been full of the filled viscoelastic agent, the front supporting portion 7*a* maintains its state under the action of the resistance of the viscoelastic agent, so that the operational reliability that the front supporting portion 7*a* is subsequently folded onto the upper surface of the optic portion 6 under the combined action of the forward movement of the optic portion 6 pushed by the push pin 9 and the side surface of the transition portion 2*b* of the implantation head 2 is ensured.

In summary, according to the present embodiment, the retaining mount 40 simultaneously functions to retain the intraocular lens 5 and improve the operational reliability of the folding of the front supporting portion 7*a*, the structural design is simple, no additional operation is required, the viscosity range of the viscoelastic agent applicable to the entire apparatus is wide. If the viscosity of the viscoelastic agent is low, the front supporting portion 7*a* is not affected by the filling of the viscoelastic agent, and the injection of the folded front supporting portion 7*a* is realized according to the normal theoretical design state. If the viscosity of the viscoelastic agent is high, the front supporting portion 7*a* is affected by the filling of the viscoelastic agent, but the guide surface 42*b* on the front surface of the retaining pin 42 of the retaining mount 40 can ensure that the front supporting portion 7*a* moves upward to be higher than the upper surface of the optic portion 6 of the intraocular lens 5, thereby improving the operational reliability of the folding of the front supporting portion 7*a* of the intraocular lens 5.

Modifications of Seventh Embodiment

For example, in the above embodiment, the guide surface 42*b* is formed by a straight slope, but the present disclosure is not limited thereto. The guide surface 42*b* may be formed by a concave or convex curved surface, or any combination of the straight slope, the concave curved surface, and the convex curved surface (for example, a plurality of straight slopes, or a combination of the straight slope and the concave curved surface), as long as the guide surface 42*b* extends obliquely upward and rearward and can guide the front supporting portion 7*a* to produce upward displacement.

In addition, in the above-described embodiment, the guide surface for guiding the front supporting portion 7*a* to be lifted rearward is formed on the retaining pin 42. However, the present disclosure is not limited to this. A detachable guide member for the front supporting portion may be provided additionally at a position between the front supporting portion 7*a* of the implanter 1 and the optic portion 6 independently from the retaining pin 42, and a front surface of the guide member for the front supporting portion forms the guide surface constituted of the slope. In addition, the specific structure of the guide member for the front supporting portion is not limited to the above embodiment, and may be any structure as long as it can guide the front supporting portion to produce upward displacement when the front supporting portion moves rearward for example due to the impact of the viscoelastic agent.

In the above embodiment, the retaining mount 40 (and the retaining pin 42) is attached to the inner packaging member 30 through the holder 41. However, the present disclosure is not limited to this. It also may be configured as a retaining mount having no attachment relationship with the inner packaging member 30, and after the intraocular lens implanter 1 is removed from the inner packaging member 30, the retaining mount (and the retaining pin thereon) is removed from the intraocular lens implanter 1 by a separate operation. It will also be seen that the inner packaging member 30 is not necessary to the preloaded intraocular lens implantation device within the spirit of the present disclosure.

In the above embodiment, the retaining mount 40 (and the retaining pin 42) are disposed at the bottom of the intraocular lens implanter 1, and the retaining pin 42 is inserted into the intraocular lens implanter 1 from the bottom to the top through the pin hole and is thus located between the front supporting portion 7*a* and the optic portion 6. However, the present disclosure is not limited thereto. The retaining mount 40 and the retaining pin 42 may also be disposed at the top of the intraocular lens implanter 1, and the pin hole is also disposed at the top of the intraocular lens implanter 1, and the retaining pin 42 is inserted into the intraocular lens implanter 1 from the top to the bottom through the pin hole and is thus located between the front supporting portion 7*a* and the optic portion 6.

Summary of the Seventh Embodiment and Modifications Thereof

In the present embodiment, the preloaded type intraocular lens implantation device comprises the intraocular lens 5 and the intraocular lens implanter 1. The intraocular lens 5 is preloaded in the intraocular lens implanter 1 and has the optic portion 6 and the front supporting portion 7*a* arranged on the front of the optic portion 6. In the intraocular lens implanter 1, the guide member for the front supporting portion is provided at a position between the optic portion 6 and the front supporting portion 7*a*, and when the front supporting portion moves rearward, the guide member for the front supporting portion can guide the front supporting portion to produce upward displacement.

With the above configuration, since the guide member for front supporting portion is provided between the optic portion 6 and the front supporting portion 7*a*, the guide member for front supporting portion can guide the front supporting portion 7*a* to produce upward displacement when the front supporting portion 7*a* moves rearward for example due to the impact of the viscoelastic agent, thereby improving the operational reliability of folding of the front supporting portion 7a onto the upper surface of the optic portion 6.

In the present embodiment, the preloaded type intraocular lens implantation device further comprises the retaining mount 40. The intraocular lens implanter 1 is formed with the pin hole 201, which is located between the optic portion 6 of the intraocular lens 5 and the front end portion 7a2 of the front supporting portion 7a in the front-rear direction. The retaining mount 40 has the retaining pin 42, which is inserted into the intraocular lens implanter 1 through the pin hole 201 and is located between the optic portion 6 of the intraocular lens 5 and the front end portion of the front supporting portion 7a to retain the intraocular lens 5 to move forward. The retaining pin 42 is the guide member for the front supporting portion.

With the above configuration, the guide member for the front supporting portion is formed by the retaining pin 41 for retaining the intraocular lens 5 to move forward, so that it is possible to reduce the number of parts, simplify the structure, and reduce the manufacturing cost.

In the present embodiment, the guide surface 42b is formed on the front surface of the retaining pin 42 facing the front support portion 7a, and this guide surface 42b is constituted by the slope extending obliquely upward and rearward.

With the above configuration, since the front surface of the retaining pin 42 facing the front end portion of the front supporting portion has the guide surface 42b, which is formed of the slope extending obliquely upward and rearward, when the front supporting portion 7a moves rearward for example due to the impact of the viscoelastic agent, it is lifted upward under the guidance of the guide surface 42b extending obliquely upward and rearward, thus improving the operational reliability of folding of the front supporting portion onto the upper surface of the optic portion.

In the present embodiment, the intraocular lens implanter 1 is formed with the filling port 202 for filling the viscoelastic agent into the interior thereof, and the filling port 202 is located in front of the front end portion 7a2 of the front supporting portion 7a in the front-rear direction.

With the present embodiment, when the viscoelastic agent filled from the filling port 202 impacts the front supporting portion 7a of the intraocular lens 5 in the rearward direction, since the retaining pin 42 located behind the front end portion 7a2 of the front supporting portion 7a has the guide surface 42b formed thereon, which is formed of the slope extending obliquely upward and rearward, the front supporting portion 7a can be guided by the guide surface 42b to produce upward displacement, thereby improving the operational reliability of folding of the front supporting portion 7a onto the upper surface of the optic portion 6.

As the slope constituting the guide surface 42b, it may be a straight surface which is straight as viewed in the left-right direction, or a curved surface which is convex or concave, or any combination of the foregoing. The front surface of the retaining pin 42 includes the vertical surface 42c on the lower side and the guide surface 42b on the upper side.

In the present embodiment, the rear surface 42a of the retaining pin 42 facing the optic portion 6 of the intraocular lens 5 is constituted by a vertical surface that is vertical when viewed from the left-right direction.

With the above configuration, the forward movement of the optic portion 6 of the intraocular lens 5 can be reliably blocked by this vertical surface 42c.

In this embodiment, the preloaded type intraocular lens implantation device further comprises the inner packaging member 30 for packaging the intraocular lens implanter 1, the retaining mount 40 further comprises the holder 41, the retaining pin 42 is integrally formed on the holder 41, and the holder 41 is mounted on the inner packaging member 30.

With the above configuration, the retaining mount 40 is mounted on the inner packaging member 40, that is, the retaining mount 40 and the inner packaging member 30 are formed separately, so that the retaining mount 40 having a complicated structure due to the retaining pin 42 can be easily manufactured.

In this embodiment, the inner packaging member 30 is a suction molded part, and the retaining mount 40 is an injection molded part. With this configuration, the retaining mount 40 is formed by injection molding different from the inner packaging member 30, and the retaining mount 40 can thus be easily manufactured.

In the present disclosure, the front supporting portion 7a and the rear supporting portion 7b project forward and rearward from the optic portion 6, respectively, and are in the form of arm having base end and free end, respectively.

In the present embodiment, the intraocular lens implanter 1 of the preloaded type intraocular lens implantation device includes: the implantation device body 3 having the intraocular lens holder 11 on which the intraocular lens 5 is disposed; the implantation head 2 for implanting the intraocular lens 5 into a human eye, wherein the implantation head 2 deforms the intraocular lens 5 when the intraocular lens 5 passes through its inner cavity, and the pin hole 201 is formed in the lower portion of the implantation head 2.

In the present embodiment, the guide surface 42b is formed at least in a portion of the front surface of the retaining pin 42 whose height is higher than the lower bottom surface of the intraocular lens holder in the vertical direction. In this way, the function of guiding the front supporting portion by the guide member can be reliably ensured.

The invention claimed is:

1. An intraocular lens implanter for implanting an intraocular lens having an optic portion into a human eye, the optic portion of the intraocular lens having a first optic portion surface and a second optic portion surface which face away from each other, the intraocular lens implanter comprising:

an implanter body having an intraocular lens holder for holding the intraocular lens;

an implantation head having a transition portion for causing the intraocular lens to undergo at least a deformation in which the intraocular lens is rolled from the side of the first optic portion surface toward the side of the second optic portion surface when the intraocular lens passes through, and a nozzle portion for implanting the intraocular lens passed through the transition portion into the human eye;

an injection member, which injects the intraocular lens from the intraocular lens holder into the human eye via the transition portion and the nozzle portion by injection operation, wherein further comprising:

a biasing member, which applies a force in a direction from the side of the second optic portion surface to the side of the first optic portion surface to the injection member by being sandwiched between the injection member and a surface of an inner cavity of the transition portion in a process that the injection member injects the intraocular lens to move in the inner cavity of the transition portion, at least when the intraocular lens leaves the intraocular lens holder, wherein the sandwiching refers to a state where the biasing member and a part of the injection member for sandwiching the biasing member contact each other and overlap in a direction perpendicular to the first optic portion surface or the second optic portion surface, and wherein the biasing member, the injection member and the inner cavity are colinear along a single line that is perpendicular to the first optic portion surface or the second optic portion surface, the injection member is assembled with the biasing member, the biasing member is driven to move together along with the injection operation of the injection member and when the biasing member moves to a predetermined position, the biasing member is stopped and when the injection member is further pushed, the injection member moves with respect to the biasing member.

2. The intraocular lens implanter of claim 1, wherein the side of the first optic portion surface is defined as a lower side, the side of the second optic portion surface is defined as an upper side, a step portion is formed between the transition portion and the intraocular lens holder, at which a lower surface of the inner cavity of the transition portion is lower than a bottom surface of the intraocular lens holder for holding the intraocular lens, the biasing member in the sandwiched state overlaps the lower surface of the inner cavity of the transition portion forming the step portion in the up-down direction.

3. The intraocular lens implanter of claim 1, wherein the biasing member is configured to be movable in a direction of the injection operation, and the surface of the inner cavity of the transition portion of the implantation head is provided with a guide portion, which has a shape approaching a movement route from rear to front along which the injection member moves when performing the injection operation, and guides the biasing member so that when moving forward, the biasing member produces displacement in a direction approaching the movement route of the injection member to be able to apply the force.

4. The intraocular lens implanter of claim 3, wherein the guide portion includes a single slope, wherein an inclination angle of the slope with respect to the movement route of the injection member is 1.5 to 25 degrees, 2.5 to 11 degrees or 3.5 to 6.5 degrees;

or at least two slopes with different inclination angles, wherein the two slopes include a first slope portion and a second slope portion, wherein the first slope portion is connected to and disposed behind the second slope portion, and the inclination angle of the second slope portion is smaller than the first slope portion;

the sandwiching refers to a state where the biasing member is sandwiched by the injection member and the second slope portion;

or a curved surface.

5. The intraocular lens implanter of claim 3, wherein the guide portion includes the first slope portion and a plane portion parallel to the movement route of the injection member, the first slope is disposed behind the plane portion, and the sandwiching refers to a state where the biasing member is sandwiched by the injection member and the plane portion.

6. The intraocular lens implanter of claim 1, wherein the biasing member has a movable portion and a fixed portion, the fixed portion and the injection member are engaged with each other in a manner capable of moving together in the direction of the injection operation in an initial state before the injection operation, and the movable portion protrudes forward in the direction of the injection operation with respect to the injection member, the movable portion is driven to move on account that the fixed portion moves together along with the injection operation of the injection member, and when the movable portion moves to a predetermined position, the biasing member is stopped, in a state where the biasing member is stopped, when the injection member is pushed forward, the engagement between the fixed portion and the injection member is released.

7. The intraocular lens implanter of claim 6, wherein the fixed portion of the biasing member is provided with a stopper protrusion, the guide portion on the surface of the inner cavity of the transition portion of the implantation head is provided with a guide groove, and the stopper protrusion can enter the guide groove to be guided by the guide groove when the biasing member moves, and the stopper protrusion is blocked by an end surface of an end of the guide groove when the stopper protrusion moves to the end of the guide groove, so that the biasing member is stopped.

8. The intraocular lens implanter of claim 6, wherein the biasing member is constituted by a flat pressing plate including a fixed piece as the fixed portion and a movable piece as the movable portion.

9. The intraocular lens implanter of claim 8, wherein the movable piece is provided with a protrusion contactable with the guide portion of the transition portion of the implantation head.

10. The intraocular lens implanter of claim 8, wherein the fixed piece is provided with a biasing protrusion protruding toward the injection member for applying the force to the injection member, and the fixed piece is connected to the movable piece via a connecting piece formed by a thin part.

11. The intraocular lens implanter of claim 1, wherein a front end portion of the injection member in a direction of the injection operation has a lens contacting portion and an extension protruding forward from the lens contacting portion, wherein the lens contacting portion is located on the side of the second optic portion surface of the intraocular lens, the extension is located on the side of the first optic portion surface, and a protrusion is formed on an upper surface of the front end portion of the injection member.

12. The intraocular lens implanter of claim 1, wherein the biasing means is further capable of applying a force in a direction from the side of the second optic portion surface toward the side the first optic portion surface to the optic portion of the intraocular lens.

13. A preloaded type intraocular lens implantation device, comprising the intraocular lens implanter of claim 1 and an intraocular lens preloaded inside the intraocular lens implanter, wherein the intraocular lens has an optic portion and a front supporting portion disposed in front of the optic portion, on the intraocular lens implanter, a guide member for the front supporting portion is disposed at a position between the optic portion and the front supporting portion, and is capable of guiding the front supporting portion to produce upward displacement when the front supporting portion moves rearward.

14. The preloaded type intraocular lens implant device of claim 13, further comprising a retaining mount, wherein the intraocular lens implanter is provided with a pin hole which is positioned between the optic portion of the intraocular lens and a front end portion of the front supporting portion in a front-rear direction, the retaining mount is provided with a retaining pin, which is inserted into the intraocular lens implanter through the pin hole and is positioned between the optic portion of the intraocular lens and the front-end portion of the front supporting portion to retain the intraocular lens to move forward, and the guide member for the front supporting portion is the retaining pin.

15. The preloaded type intraocular lens implantation device of claim 14, wherein a guide surface is formed on a front surface of the retaining pin facing the front supporting portion, the guide surface being constituted by a slope extending obliquely upward and rearward.

16. The intraocular lens implanter of claim 1, wherein an end of the biasing member facing the nozzle portion is configured to orient the first optic portion surface before being sandwiched and when it is not in contact with the upper surface of the inner cavity of the transition portion.

\* \* \* \* \*